US012780792B2

(12) United States Patent
Stoicescu

(10) Patent No.: US 12,780,792 B2
(45) Date of Patent: Nov. 3, 2026

(54) HETEROCYCLIC COMPOUNDS

(71) Applicant: FLORATEK PHARMA S.A., Aubonne (CH)

(72) Inventor: Dan Florin Stoicescu, Aubonne (CH)

(73) Assignee: FLORATEK PHARMA S.A., Aubonne (CH)

( * ) Notice: Subject to any disclaimer, the term of this patent is extended or adjusted under 35 U.S.C. 154(b) by 440 days.

(21) Appl. No.: 18/288,743

(22) PCT Filed: Apr. 29, 2022

(86) PCT No.: PCT/EP2022/061545
§ 371 (c)(1),
(2) Date: Oct. 27, 2023

(87) PCT Pub. No.: WO2022/229417
PCT Pub. Date: Nov. 3, 2022

(65) Prior Publication Data
US 2024/0239762 A1 Jul. 18, 2024

(30) Foreign Application Priority Data
Apr. 29, 2021 (GB) ..................................... 2106130

(51) Int. Cl.
*C07D 311/80* (2006.01)
*A61K 31/352* (2006.01)
*A61P 21/00* (2006.01)

(52) U.S. Cl.
CPC .......... *C07D 311/80* (2013.01); *A61K 31/352* (2013.01); *A61P 21/00* (2018.01)

(58) Field of Classification Search
CPC ...... C07D 311/80; A61P 21/00; A61K 31/352
See application file for complete search history.

(56) References Cited

U.S. PATENT DOCUMENTS 12,264,142 B2 * 4/2025 Stoicescu ............. C07D 311/80
2011/0021618 A1 1/2011 Sherris
2012/0069289 A1 3/2012 Taugerbeck et al.

FOREIGN PATENT DOCUMENTS

WO 2015/147247 A1 10/2015
WO 2021/078811 A1 4/2021

OTHER PUBLICATIONS

International search report and written opinion for application No. PCT/EP2022/061545 mailed Aug. 18, 2022.

* cited by examiner

*Primary Examiner* — Kamal A Saeed
(74) *Attorney, Agent, or Firm* — Lando & Anastasi, LLP

(57) ABSTRACT

The present invention concerns compounds of Formula (1), pharmaceutically acceptable salts, solvates or prodrugs thereof, pharmaceutical compositions comprising the same, and the use of the same in treating or preventing a disease.

(1)

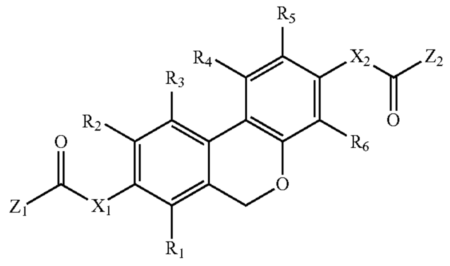

9 Claims, 6 Drawing Sheets

HETEROCYCLIC COMPOUNDS

CLAIM OF PRIORITY

This application is a U.S. national phase application and claims the benefit of priority under 35 U.S.C § 371 of International Application No. PCT/EP2022/061545, filed on Apr. 29, 2022, which claims priority to Foreign Application No. GB 2106130.4, filed Apr. 29, 2021. The disclosure of each of the foregoing applications is incorporated herein by reference in its entirety.

The present invention relates to compounds of Formula (1), and to associated salts, solvates, and prodrugs thereof as well as pharmaceutical compositions comprising the same. The present invention also relates to the use of such compounds and compositions in the treatment and prevention of medical disorders and diseases.

BACKGROUND OF THE INVENTION

Polyphenols and their derivatives are usually present in plants and human diets. They show various bio active effects including anti-viral, anti-inflammatory, cardioprotective, anti-diabetic, anti-cancer, anti-aging, etc. Their basic structures consist of 2 to 4 aromatic rings with different substitution patterns.

While the great majority of polyphenols exhibit low toxicity, because of their major drawbacks—poor bio-availability and lack of selectivity—there is a need for rationally designed new chemical entities, that could achieve in the future the translation from bench to bedside.

SUMMARY OF INVENTION

A first aspect of the invention provides compound of formula (1):

Formula (1)

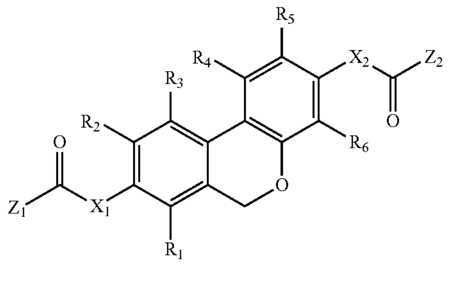

wherein:

$X_1$ and $X_2$, independently, are selected from —O—, —S—, —NH—, —$NHCH_2$—, —NR, —$CH_2$—, and —CHR—;

R is independently selected from $C_1$-$C_6$ alkyl, $C_2$-$C_6$ alkenyl, $C_2$-$C_6$ alkynyl, —OH, and —$OR^\beta$;

$R^1$, $R^2$, $R^3$, $R^4$, $R^5$, and $R^6$, independently, are selected from H; halo; —CN; —$NO_2$; —$R^\beta$; —OH; —$OR^\beta$; —SH; —$SR^\beta$; —$SOR^\beta$; —$SO_2H$; —$SO_2R^\beta$; —$SO_2NH_2$; —$SO_2NHR^\beta$; —$SO_2N(RP)_2$; —$NH_2$; —$NHR^\beta$; —$N(R^\beta)_2$; —CHO; —$COR^\beta$; —COOH; —$COOR^\beta$; and —$OCOR^\beta$;

each —$R^\beta$ is independently selected from a $C_1$-$C_6$ alkyl, $C_2$-$C_6$ alkenyl, $C_2$-$C_6$ alkynyl or $C_3$-$C_{14}$ cyclic group; wherein any —$R^\beta$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —$NO_2$, —C≡CH, —CHO, —$CON(CH_3)_2$ or oxo (=O) groups;

$Z^1$ and $Z^2$, independently, are selected from —$NR^7R^8$ and —$OR^9$; $R^7$, $R^8$, and $R^9$, independently, are selected from H, $C_1$-$C_6$ alkyl, $C_2$-$C_6$ alkenyl, $C_2$-$C_6$ alkynyl or $C_3$-$C_{14}$ cyclic group; wherein any $R^7$, $R^8$ or $R^9$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —$NO_2$, —C≡CH, —CHO, —$CON(CH_3)_2$ or oxo (=O) groups.

A second aspect of the invention provides a compound of Formula (A) or Formula (B):

(A)

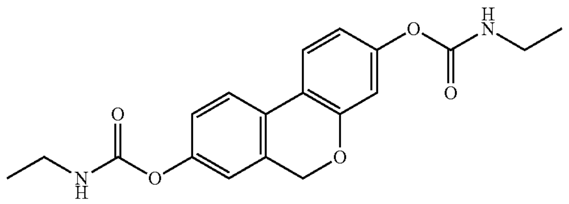

(B)

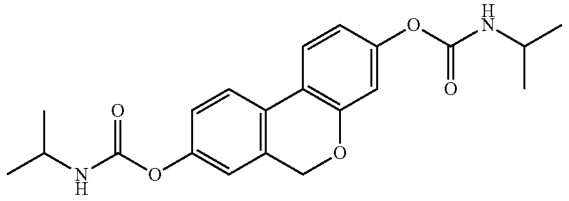

A third aspect of the invention provides pharmaceutically acceptable salt, solvate or prodrug of the compound of the first or second aspect of the invention.

A fourth aspect of the invention provides a pharmaceutical composition comprising a compound of the first or second aspect of the invention, or a pharmaceutically acceptable salt, solvate or prodrug of the third aspect of the invention, and a pharmaceutically acceptable excipient.

A fifth aspect of the invention provides a compound of the first or second aspect of the invention, or a pharmaceutically acceptable salt, solvate or prodrug of the third aspect of the invention, or a pharmaceutical composition of the fourth aspect of the invention, for use in medicine, and/or for use in the treatment or prevention of a disease, disorder or condition. In one embodiment, the disease, disorder or condition is selected from the group consisting of mitochondrial diseases (including for example poor growth, loss of muscle coordination, muscle weakness, visual problems, hearing problems, heart disease, liver disease, kidney disease, gastrointestinal disorders, respiratory disorders, neurological problems, metabolic syndrome, cardiovascular disease, sarcopenia, muscle degenerative disease, liver diseases, nonalcoholic fatty liver disease (NAFLD), nonalcoholic steatohepatitis (NASH), ischemia/reperfusion injury, inflammatory bowel disease, Crohn's disease, type II diabetes mellitus, hyperlipidemia, neurodegenerative disease, Alzheimer's disease, Parkinson's disease, Huntington's disease, anxiety disorder, cancer.

A sixth aspect of the invention provides the use of a compound of the first or second aspect, a pharmaceutically effective salt, solvate or prodrug of the third aspect, or a pharmaceutical composition according to the fourth aspect, in the manufacture of a medicament for the treatment or prevention of a disease, disorder or condition. Typically the treatment or prevention comprises the administration of the compound, salt, solvate, prodrug or pharmaceutical composition to a subject. In one embodiment, the disease, disorder or condition is selected from the group consisting of mitochondrial diseases (including for example poor growth, loss of muscle coordination, muscle weakness, visual problems, hearing problems, heart disease, liver disease, kidney disease, gastrointestinal disorders, respiratory disorders, neurological problems, metabolic syndrome, cardiovascular disease, sarcopenia, muscle degenerative disease, liver diseases, nonalcoholic fatty liver disease (NAFLD), nonalcoholic steatohepatitis (NASH), ischemia/reperfusion injury, inflammatory bowel disease, Crohn's disease, type II diabetes mellitus, hyperlipidemia, neurodegenerative disease, Alzheimer's disease, Parkinson's disease, Huntington's disease, anxiety disorder, cancer.

A seventh aspect of the invention provides a method of treatment or prevention of a disease, disorder or condition, the method comprising the step of administering an effective amount of a compound of the first or second aspect, or a pharmaceutically acceptable salt, solvate or prodrug of the third aspect, or a pharmaceutical composition of the fourth aspect, to thereby treat or prevent the disease, disorder or condition. Typically the administration is to a subject in need thereof. In one embodiment, the disease, disorder or condition is selected from the group consisting of mitochondrial diseases (including for example poor growth, loss of muscle coordination, muscle weakness, visual problems, hearing problems, heart disease, liver disease, kidney disease, gastrointestinal disorders, respiratory disorders, neurological problems, metabolic syndrome, cardiovascular disease, sarcopenia, muscle degenerative disease, liver diseases, nonalcoholic fatty liver disease (NAFLD), nonalcoholic steatohepatitis (NASH), ischemia/reperfusion injury, inflammatory bowel disease, Crohn's disease, type II diabetes mellitus, hyperlipidemia, neurodegenerative disease, Alzheimer's disease, Parkinson's disease, Huntington's disease, anxiety disorder, cancer.

DEFINITIONS

Figure 1:
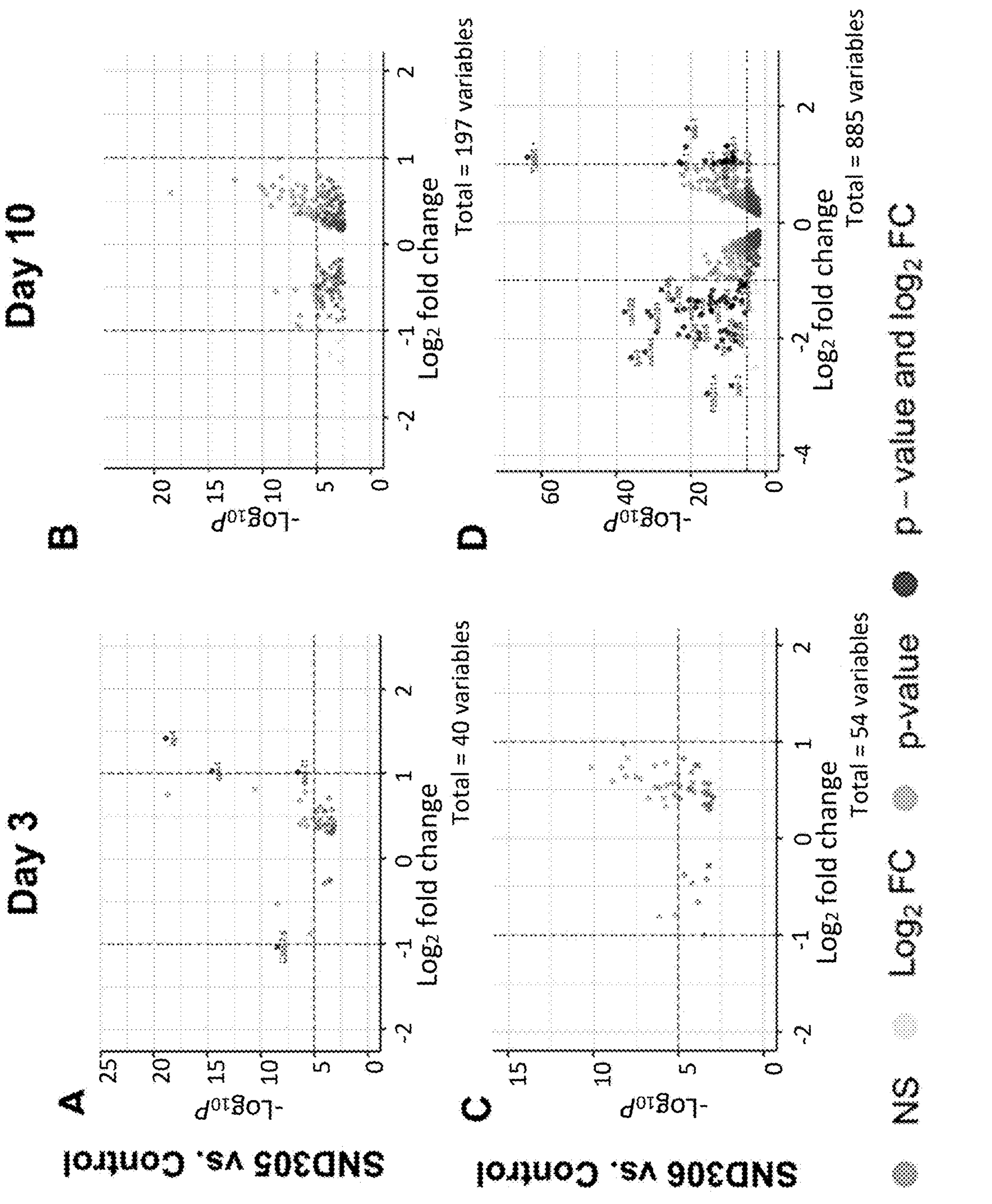
FIG. 1 shows the volcano plots for all three comparison groups in connection with SND305 and SND306. Dots indicate differential gene expression that exceeds defined significance and fold-change thresholds. Thresholds are based on convention—biologically relevant groups of genes may be just below the arbitrary cutoffs for logFC or P value.

In the context of the present specification, a "hydrocarbyl" substituent group or a hydrocarbyl moiety in a substituent group only includes carbon and hydrogen atoms but, unless stated otherwise, does not include any heteroatoms, such as N, O or S, in its carbon skeleton. A hydrocarbyl group/moiety may be saturated or unsaturated (including aromatic), and may be straight-chained or branched, or be or include cyclic groups wherein, unless stated otherwise, the cyclic group does not include any heteroatoms, such as N, O or S, in its carbon skeleton. Examples of hydrocarbyl groups include alkyl, alkenyl, alkynyl, cycloalkyl, cycloalkenyl and aryl groups/moieties and combinations of all of these groups/moieties. Typically a hydrocarbyl group is a $C_1$-$C_{12}$ hydrocarbyl group. More typically a hydrocarbyl group is a $C_1$-$C_{10}$ hydrocarbyl group. A "hydrocarbylene" group is similarly defined as a divalent hydrocarbyl group.

An "alkyl" substituent group or an alkyl moiety in a substituent group may be linear or branched. Examples of alkyl groups/moieties include methyl, ethyl, n-propyl, i-propyl, n-butyl, i-butyl, t-butyl and n-pentyl groups/moieties. Unless stated otherwise, the term "alkyl" does not include "cycloalkyl". Typically an alkyl group is a $C_1$-$C_{12}$ alkyl group. More typically an alkyl group is a $C_1$-$C_6$ alkyl group. An "alkylene" group is similarly defined as a divalent alkyl group.

An "alkenyl" substituent group or an alkenyl moiety in a substituent group refers to an unsaturated alkyl group or moiety having one or more carbon-carbon double bonds. Examples of alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1,4-hexadienyl groups/moieties. Unless stated otherwise, the term "alkenyl" does not include "cycloalkenyl". Typically an alkenyl group is a $C_2$-$C_{12}$ alkenyl group. More typically an alkenyl group is a $C_2$-$C_6$ alkenyl group. An "alkenylene" group is similarly defined as a divalent alkenyl group.

An "alkynyl" substituent group or an alkynyl moiety in a substituent group refers to an unsaturated alkyl group or moiety having one or more carbon-carbon triple bonds. Examples of alkynyl groups/moieties include ethynyl, propargyl, but-1-ynyl and but-2-ynyl. Typically an alkynyl group is a $C_2$-$C_{12}$ alkynyl group. More typically an alkynyl group is a $C_2$-$C_6$ alkynyl group. An "alkynylene" group is similarly defined as a divalent alkynyl group.

A "haloalkyl" substituent group or haloalkyl group in a substituent group refers to an alkyl, alkenyl, or alkynyl substituent group or moiety including one or more carbon atoms and one or more halo atoms, e.g. Cl, Br, I, or F. Each halo atom replaces a hydrogen of the alkyl, alkenyl, or alkynyl substituent group or moiety. Examples include $—CH_2F—CHF_2$, $—CHI_2$, $—CHBr_2$, $—CHCl_2$, $—CF_3$, $—CH_2CF_3$ and $CF_2CH_3$. Suitable haloalkyls include but are not limited to $—CF_3$, and $—CH_2CF_3$.

An "alkoxy" substituent group or alkoxy group in a substituent group refers to an alkyl, alkenyl, or alkynyl substituent group or moiety including one or more carbon atoms and one or more oxygen atoms. Each oxygen atom replaces a carbon atom (for example the terminal or bonding carbon) of the alkyl, alkenyl, or alkynyl substituent group or moiety. Examples include $—OCH_3$, $—OCH_2CH_3$, $—OCH_2CH_2CH_3$, and $—OCH(CH_3)(CH_3)$.

An "alkylthio" substituent group or alkylthio group in a substituent group refers to an alkyl, alkenyl, or alkynyl substituent group or moiety including one or more carbon atoms and one or more sulphur atoms. Each sulphur atom replaces a carbon atom (for example the terminal or bonding carbon) of the alkyl, alkenyl, or alkynyl substituent group or moiety. Examples include $—SCH_3$, $—SCH_2CH_3$, $—SCH_2CH_2CH_3$, and $—SCH(CH_3)(CH_3)$.

An "alkylsulfinyl" substituent group or alkylsulfinyl group in a substituent group refers to an alkyl, alkenyl, or alkynyl substituent group or moiety including one or more carbon atoms and one or more sulfinyl groups ($—S(═O)—$). Each sulfinyl group replaces a carbon atom (for example the terminal or bonding carbon) of the alkyl, alkenyl, or alkynyl substituent group or moiety. Examples include $—S(═O)CH_3$, $—S(═O)CH_2CH_3$, $—S(═O)CH_2CH_2CH_3$, and $—S(═O)CH(CH_3)(CH_3)$.

An "alkylsulfonyl" substituent group or alkylsulfonyl group in a substituent group refers to an alkyl, alkenyl, or alkynyl substituent group or moiety including one or more carbon atoms and one or more sulfonyl groups ($—SO_2—$). Each sulfonyl group replaces a carbon atom (for example the terminal or bonding carbon) of the alkyl, alkenyl, or alkynyl substituent group or moiety. Examples include $—SO_2(CH_3)$, $—SO_2(CH_2CH_3)$, $—SO_2(CH_2CH_2CH_3)$, and $—SO_2(CH(CH_3)(CH_3))$.

An "arylsulfonyl" substituent group or arylsulfonyl group in a substituent group refers to an aryl substituent group or moiety including one or more carbon atoms and one or more sulfonyl groups ($—SO_2—$). Each sulfonyl group replaces a carbon atom (for example the terminal or bonding carbon) of the alkyl, alkenyl, or alkynyl substituent group or moiety. Examples include $—SO_2(CH_3)$, $—SO_2(CH_2CH_3)$, $—SO_2(CH_2CH_2CH_3)$, and $—SO_2(CH(CH_3)(CH_3))$.

A "cyclic" substituent group or a cyclic moiety in a substituent group refers to any hydrocarbyl ring, wherein the hydrocarbyl ring may be saturated or unsaturated and may include one or more heteroatoms, e.g. N, O or S, in its carbon skeleton. Examples of cyclic groups include aliphatic cyclic, cycloalkyl, cycloalkenyl, heterocyclic, aryl and heteroaryl groups as discussed below. A cyclic group may be monocyclic, bicyclic (e.g. bridged, fused or spiro), or polycyclic. Typically, a cyclic group is a 3- to 12-membered cyclic group, which means it contains from 3 to 12 ring atoms. More typically, a cyclic group is a 3- to 7-membered monocyclic group, which means it contains from 3 to 7 ring atoms.

A "heterocyclic" substituent group or a heterocyclic moiety in a substituent group refers to a cyclic group or moiety including one or more carbon atoms and one or more heteroatoms, e.g. N, O or S, in the ring structure. Examples of heterocyclic groups include heteroaryl groups as discussed below and non-aromatic heterocyclic groups such as azetidinyl, azetinyl, tetrahydrofuranyl, pyrrolidinyl, tetrahydrothiophenyl, tetrahydropyranyl, piperidinyl, piperazinyl, morpholinyl and thiomorpholinyl groups.

An "aliphatic cyclic" substituent group or aliphatic cyclic moiety in a substituent group refers to a hydrocarbyl cyclic group or moiety that is not aromatic. The aliphatic cyclic group may be saturated or unsaturated and may include one or more heteroatoms, e.g. N, O or S, in its carbon skeleton. Examples include cyclopropyl, cyclohexyl and morpholinyl. Unless stated otherwise, an aliphatic cyclic substituent group or moiety may include monocyclic, bicyclic or polycyclic hydrocarbyl rings.

A "cycloalkyl" substituent group or a cycloalkyl moiety in a substituent group refers to a saturated hydrocarbyl ring containing, for example, from 3 to 7 carbon atoms, examples of which include cyclopropyl, cyclobutyl, cyclopentyl and cyclohexyl. Unless stated otherwise, a cycloalkyl substituent group or moiety may include monocyclic, bicyclic or polycyclic hydrocarbyl rings.

A "cycloalkenyl" substituent group or a cycloalkenyl moiety in a substituent group refers to a non-aromatic unsaturated hydrocarbyl ring having one or more carbon-carbon double bonds and containing, for example, from 3 to 7 carbon atoms, examples of which include cyclopent-1-en-1-yl, cyclohex-1-en-1-yl and cyclohex-1,3-dien-1-yl. Unless stated otherwise, a cycloalkenyl substituent group or moiety may include monocyclic, bicyclic or polycyclic hydrocarbyl rings.

An "aryl" substituent group or an aryl moiety in a substituent group refers to an aromatic hydrocarbyl ring. The term "aryl" includes monocyclic aromatic hydrocarbons and polycyclic fused ring aromatic hydrocarbons wherein all of the fused ring systems (excluding any ring systems which are part of or formed by optional substituents) are aromatic.

Examples of aryl groups/moieties include phenyl, naphthyl, anthracenyl and phenanthrenyl. Unless stated otherwise, the term “aryl” does not include “heteroaryl”.

A “heteroaryl” substituent group or a heteroaryl moiety in a substituent group refers to an aromatic heterocyclic group or moiety. The term “heteroaryl” includes monocyclic aromatic heterocycles and polycyclic fused ring aromatic heterocycles wherein all of the fused ring systems (excluding any ring systems which are part of or formed by optional substituents) are aromatic. Examples of heteroaryl groups/moieties include the following:

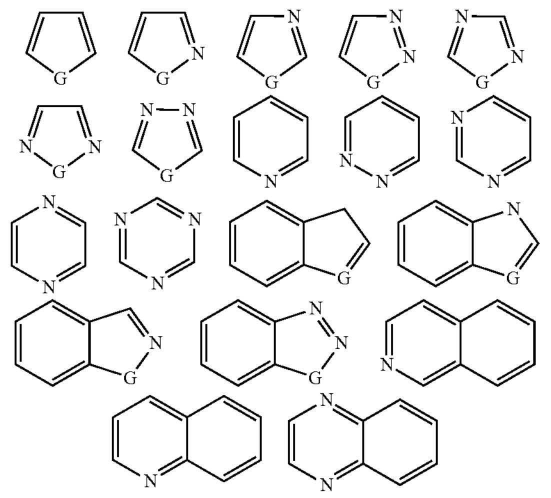

wherein G=O, S or NH.

For the purposes of the present specification, where a combination of moieties is referred to as one group, for example, arylalkyl, arylalkenyl, arylalkynyl, alkylaryl, alkenylaryl or alkynylaryl, the last mentioned moiety contains the atom by which the group is attached to the rest of the molecule. An example of an arylalkyl group is benzyl.

Typically a substituted group comprises 1, 2, 3 or 4 substituents, more typically 1, 2 or 3 substituents, more typically 1 or 2 substituents, and even more typically 1 substituent.

Unless stated otherwise, any divalent bridging substituent (e.g. —O—, —S—, —NH—, —N($R^β$)— or —$R^α$—) of an optionally substituted group or moiety must only be attached to the specified group or moiety and may not be attached to a second group or moiety, even if the second group or moiety can itself be optionally substituted.

The term “halo” includes fluoro, chloro, bromo and iodo.

Where reference is made to a carbon atom of a group being replaced by an N, O or S atom, what is intended is that:

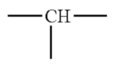

is replaced by

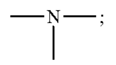

—$CH_2$— is replaced by —NH—, —O— or —S—;

—$CH_3$ is replaced by —$NH_2$, —OH, or —SH;

—CH= is replaced by —N=;

$CH_2$= is replaced by NH=, O= or S=; or

CH≡ is replaced by N≡.

In the context of the present specification, unless otherwise stated, a $C_x$-$C_y$ group is defined as a group containing from x to y carbon atoms. For example, a $C_1$-$C_4$ alkyl group is defined as an alkyl group containing from 1 to 4 carbon atoms. Optional substituents and moieties are not taken into account when calculating the total number of carbon atoms in the parent group substituted with the optional substituents and/or containing the optional moieties. For the avoidance of doubt, replacement heteroatoms, e.g. N, O or S, are counted as carbon atoms when calculating the number of carbon atoms in a $C_x$-$C_y$ group. For example, a morpholinyl group is to be considered a $C_6$ heterocyclic group, not a $C_4$ heterocyclic group.

A “protecting group” refers to a grouping of atoms that when attached to a reactive functional group (e.g. OH) in a compound masks, reduces or prevents reactivity of the functional group.

In the context of the present specification, = is a double bond; ≡ is a triple bond.

DETAILED DESCRIPTION

A first aspect of the invention provides a compound of formula 1):

Formula (1)

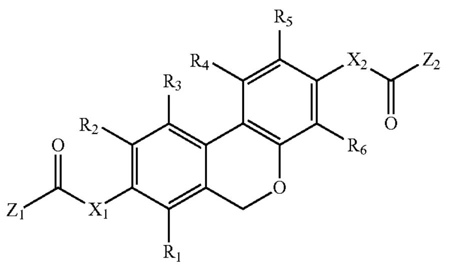

wherein:

$X_1$ and $X_2$, independently, are selected from —O—, —S—, —NH—, —$NHCH_2$—, —NR, —$CH_2$—, and —CHR—;

R is independently selected from $C_1$-$C_6$ alkyl, $C_2$-$C_6$ alkenyl, $C_2$-$C_6$ alkynyl, —OH, and —$OR^β$;

$R^1$, $R^2$, $R^3$, $R^4$, $R^5$, and $R^6$, independently, are selected from H; halo; —CN; —$NO_2$; —$R^β$; —OH; —$OR^β$; —SH; —$SR^β$; —$SOR^β$; —$SO_2H$; —$SO_2R^β$; —$SO_2NH_2$; —$SO_2NHR^β$; —$SO_2N(RP)_2$; —$NH_2$; —$NHR^β$; —$N(R^β)_2$; —CHO; —$COR^β$; —COOH; —$COOR^β$; and —$OCOR^β$;

each —$R^β$ is independently selected from a $C_1$-$C_6$ alkyl, $C_2$-$C_6$ alkenyl, $C_2$-$C_6$ alkynyl or $C_3$-$C_{14}$ cyclic group; wherein any —$R^β$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —$NO_2$, —C≡CH, —CHO, —$CON(CH_3)_2$ or oxo (=O) groups;

$Z^1$ and $Z^2$, independently, are selected from —$NR^7R^8$ and —$OR^9$;

$R^7$, $R^8$, and $R^9$, independently, are selected from H, $C_1$-$C_6$ alkyl, $C_2$-$C_6$ alkenyl, $C_2$-$C_6$ alkynyl or $C_3$-$C_{14}$ cyclic group;

wherein any $R^7$, $R^8$ or $R^9$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —$NO_2$, —C≡CH, —CHO, —$CON(CH_3)_2$ or oxo (=O) groups.

In one embodiment, $X_1$ and $X_2$, independently, are selected from —O—, —S—, —NH—, and —$CH_2$—.

In one embodiment, $X_1$ and $X_2$, independently, are selected from —O— and —$CH_2$—.

In one embodiment, $X_1$ and $X_2$ are —O—.

In one embodiment, R is a $C_1$-$C_6$ alkyl, such as a $C_1$-$C_4$ alkyl.

In one embodiment, R is methyl.

In one embodiment, $R^1$, $R^2$, $R^3$, $R^4$, $R^5$, and $R^6$, independently, are selected from H; halo; —CN; —$NO_2$; —OH; —SH; —$SO_2$H; —$SO_2NH_2$; —$NH_2$; —CHO; and —COOH.

In one embodiment, $R^1$, $R^2$, $R^3$, $R^4$, $R^5$, and $R^6$, independently, are selected from H; halo; —CN; —$NO_2$; —OH; —$NH_2$; —CHO; and —COOH.

In one embodiment, $R^1$, $R^2$, $R^3$, $R^4$, $R^5$, and $R^6$, independently, are selected from H; halo; —CN; —$NO_2$; —OH; and —$NH_2$.

In one embodiment, $R^1$, $R^2$, $R^3$, $R^4$, $R^5$, and $R^6$ are H.

In one embodiment, $R^7$, $R^8$, and $R^9$, independently, are selected from H, $C_1$-$C_6$ alkyl, $C_2$-$C_6$ alkenyl, and $C_2$-$C_6$ alkynyl.

In one embodiment, $Z^1$ and $Z^2$, independently, are selected from —$NR^7R^8$, wherein $R^7$, and $R^8$, are as defined above. For example, $R^7$, and $R^8$, may independently be selected from H, $C_1$-$C_6$ alkyl, and $C_2$-$C_6$ alkenyl. For example, $R^7$, and $R^8$, may independently be selected from H, and $C_1$-$C_6$ alkyl. For example, $R^7$, and $R^8$, may independently be selected from H, and $C_1$-$C_4$ alkyl.

In one embodiment, $Z^1$ and $Z^2$, independently, are selected from —$NHR^8$, wherein $R^8$ is as defined above. For example, $R^8$ may be selected from $C_{1-6}$ alkyl and $C_2$-$C_6$ alkenyl. For example, $R^8$ may be selected from $C_{1-6}$ alkyl. For example, $R^8$ may be selected from $C_{1-4}$ alkyl. For example, $R^8$ may be selected from $C_{1-3}$ alkyl, such as methyl or ethyl. Alternatively, $R^8$ may be propyl, such as i-propyl.

In one embodiment, $Z^1$ and $Z^2$ are independently selected from —$NHCH_3$, —$NHCH_2CH_3$, and —$NHCH(CH_3)_2$.

In one embodiment, $Z^1$ and $Z^2$ are both —$NHCH_3$.

In one embodiment, $Z^1$ and $Z^2$ are both —$NHCH_2CH_3$.

In one embodiment, $Z^1$ and $Z^2$ are both —$NHCH(CH_3)_2$.

In one embodiment, $R^1$, $R^2$, $R^3$, $R^4$, $R^5$, and $R^6$, independently, are selected from H; halo; —CN; —$NO_2$; —OH; —SH; —$SO_2$H; —$SO_2NH_2$; —$NH_2$; —CHO; and —COOH; $Z^1$ and $Z^2$, independently, are selected from —$NR^7R^8$; and $R^7$, and $R^8$, independently, are selected from H, $C_1$-$C_6$ alkyl, $C_2$-$C_6$ alkenyl, and $C_2$-$C_6$ alkynyl. For example, $R^7$, and $R^8$ may be selected from $C_{1-4}$ alkyl, such as methyl or ethyl or propyl. In one embodiment, $Z^1$ and $Z^2$ are both —$NHCH(CH_3)_2$. In one embodiment, $Z^1$ and $Z^2$ are both —$NHCH_2CH_3$.

In one embodiment, $X_1$ and $X_2$, independently, are selected from —O—, and —$CH_2$—; $R^1$, $R^2$, $R^3$, $R^4$, $R^5$, and $R^6$, independently, are selected from H; halo; —CN; —$NO_2$; —$R^\beta$; —OH; —$OR^\beta$; —SH; —$SR^\beta$; —$SOR^\beta$; —$SO_2$H; —$SO_2R^\beta$; —$SO_2NH_2$; —$SO_2NHR^\beta$; —$SO_2N(RP)_2$; —$NH_2$; —$NHR^\beta$; —$N(RD)_2$; —CHO; —$COR^\beta$; —COOH; —$COOR^\beta$; and —$OCOR^\beta$; each —$R^3$ is independently selected from a $C_1$-$C_6$ alkyl, $C_2$-$C_6$ alkenyl, $C_2$-$C_6$ alkynyl or $C_3$-$C_{14}$ cyclic group; wherein any —$R^\beta$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —$NO_2$, —C≡CH, —CHO, —$CON(CH_3)_2$ or oxo (=O) groups;

$Z^1$ and $Z^2$, independently, are selected from —$NR^7R^8$ and —$OR^9$;

$R^7$, $R^8$, and $R^9$, independently, are selected from H, $C_1$-$C_6$ alkyl, $C_2$-$C_6$ alkenyl, $C_2$-$C_6$ alkynyl or $C_3$-$C_{14}$ cyclic group; wherein any $R^7$, $R^8$ or $R^9$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —$NO_2$, —C≡CH, —CHO, —$CON(CH_3)_2$ or oxo (=O) groups.

In one embodiment, $X_1$ and $X_2$, independently, are selected from —O—, and —$CH_2$—; $R^1$, $R^2$, $R^3$, $R^4$, $R^5$, and $R^6$, independently, are selected from H; halo; —CN; —$NO_2$; —OH; —SH; —$SO_2$H; —$SO_2NH_2$; —$NH_2$; —CHO; and —COOH; $Z^1$ and $Z^2$, independently, are selected from —$NR^7R^8$; and $R^7$, and $R^8$, independently, are selected from H, $C_1$-$C_6$ alkyl, $C_2$-$C_6$ alkenyl, and $C_2$-$C_6$ alkynyl.

In one embodiment, $X_1$ and $X_2$, independently, are selected from —O—, and —$CH_2$—; $R^1$, $R^2$, $R^3$, $R^4$, $R^5$, and $R^6$, independently, are selected from H; halo; —CN; —$NO_2$; —SH; and —$NH_2$; $Z^1$ and $Z^2$, independently, are selected from —$NR^7R^8$; and $R^7$, and $R^8$, independently, are selected from H, $C_1$-$C_6$ alkyl, $C_2$-$C_6$ alkenyl, and $C_2$-$C_6$ alkynyl.

In one embodiment, $X_1$ and $X_2$, independently, are selected from —O—, and —$CH_2$—; $R^1$, $R^2$, $R^3$, $R^4$, $R^5$, and $R^6$, independently, are selected from H; halo; and —CN; $Z^1$ and $Z^2$, independently, are selected from —$NR^7R^8$; and $R^7$, and $R^8$, independently, are selected from H, and $C_1$-$C_6$ alkyl.

In one embodiment, $X_1$ and $X_2$, independently, are selected from —O—, and —$CH_2$—; $R^1$, $R^2$, $R^3$, $R^4$, $R^5$, and $R^6$, independently, are selected from H; halo; and —CN; $Z^1$ and $Z^2$, independently, are selected from —$NHR^8$; and $R^8$ is selected from H, and $C_1$-$C_6$ alkyl.

In one embodiment, the compound of formula (1) is a compound of formula (2):

(2)

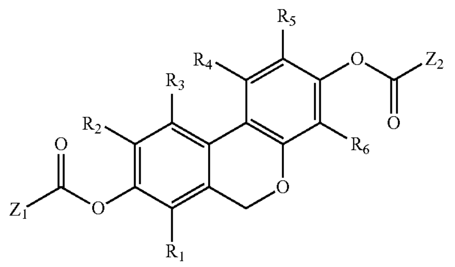

wherein:

$Z^1$ and $Z^2$, independently, are selected from —$NR^7R^8$ and —$OR^9$, $R^1$, $R^2$, $R^3$, $R^4$, $R^5$, and $R^6$, independently, are selected from H; halo; —CN; —$NO_2$; —$R^\beta$; —OH; —$OR^\beta$; —SH; —$SR^\beta$; —$SOR^\beta$; —$SO_2$H; —$SO_2R^\beta$; —$SO_2NH_2$; —$SO_2NHR^\beta$; —$SO_2N(RP)_2$; —$NH_2$; —$NHR^\beta$; —$N(RD)_2$; —CHO; —$COR^\beta$; —COOH; —$COOR^\beta$; and —$OCOR^\beta$; each —$R^\beta$ is independently selected from a $C_1$-$C_6$ alkyl, $C_2$-$C_6$ alkenyl, $C_2$-$C_6$ alkynyl or $C_3$-$C_{14}$ cyclic group; wherein any —$R^\beta$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —$NO_2$, —C≡CH, —CHO, —$CON(CH_3)_2$ or oxo (=O) groups;

$R^7$, $R^8$, and $R^9$, independently, are selected from H, $C_1$-$C_6$ alkyl, $C_2$-$C_6$ alkenyl, $C_2$-$C_6$ alkynyl or $C_3$-$C_{14}$ cyclic group; wherein any $R^7$, $R^8$ or $R^9$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —$NO_2$, —C≡CH, —CHO, —CON$(CH_3)_2$ or oxo (=O) groups.

In one embodiment, the compound is a compound of formula (2) in which $R^1$, $R^2$, $R^3$, $R^4$, $R^5$, and $R^6$, independently, are selected from H; halo; —CN; —$NO_2$; —OH; —SH; —$SO_2H$; —$SO_2NH_2$; —$NH_2$; —CHO; and —COOH. For example, in one embodiment, $R^1$, $R^2$, $R^3$, $R^4$, $R^5$, and $R^6$ are H.

In one embodiment, the compound is a compound of formula (2) in which $Z^1$ and $Z^2$, independently, are selected from —$NR^7R^8$, wherein $R^7$, and $R^8$, are as defined above. For example, $R^7$, and $R^8$, may independently be selected from H, $C_1$-$C_6$ alkyl, and $C_2$-$C_6$ alkenyl. For example, $R^7$, and $R^8$, may independently be selected from H, and $C_1$-$C_6$ alkyl. For example, $R^7$, and $R^8$, may independently be selected from H, and $C_1$-$C_4$ alkyl. For example, $R^7$, and $R^8$, may independently be selected from H and $C_{1-3}$ alkyl, such as methyl or ethyl. Alternatively, $R^8$ may be propyl, such as i-propyl.

In one embodiment, the compound is a compound of formula (2) in which $Z^1$ and $Z^2$, independently, are selected from —$NHR^8$, wherein $R^8$ is as defined above. For example, $R^8$ may be selected from $C_1$-6 alkyl and $C_2$-$C_6$ alkenyl. For example, $R^8$ may be selected from $C_{1-6}$ alkyl. For example, $R^8$ may be selected from $C_{1-4}$ alkyl. For example, $R^8$ may be selected from $C_{1-3}$ alkyl, such as methyl or ethyl. Alternatively, $R^8$ may be propyl, such as i-propyl.

In one embodiment, the compound is a compound of formula (2) in which $Z^1$ and $Z^2$ are independently selected from —$NHCH_3$, —$NHCH_2CH_3$, and —$NHCH(CH_3)_2$.

In one embodiment, the compound is a compound of formula (2) in which $Z^1$ and $Z^2$ are both —$NHCH_3$.

In one embodiment, the compound is a compound of formula (2) in which $Z^1$ and $Z^2$ are both —$NHCH_2CH_3$.

In one embodiment, the compound is a compound of formula (2) in which $Z^1$ and $Z^2$ are both —$NHCH(CH_3)_2$.

In one embodiment, the compound is a compound of formula (2) in which $Z^1$ and $Z^2$, independently, are selected from —$NR^7R^8$. For example, in one embodiment, $R^7$, $R^8$, and $R^9$, independently, are selected from H, $C_1$-$C_6$ alkyl, $C_2$-$C_6$ alkenyl, and $C_2$-$C_6$ alkynyl. For example, in one embodiment, $Z^1$ and $Z^2$, independently, are selected from —$NHR^8$, wherein $R^8$ is as defined above. For example, $R^8$ may be selected from $C_{1-4}$ alkyl, such as methyl or ethyl or propyl. In one embodiment, $Z^1$ and $Z^2$ are independently selected from —$NHCH(CH_3)_2$ and —$NHCH_2CH_3$.

In one embodiment, the compound is a compound of formula (2) in which $R^1$, $R^2$, $R^3$, $R^4$, $R^5$, and $R^6$, independently, are selected from H; halo; —CN; —$NO_2$; —OH; —SH; —$SO_2H$; —$SO_2NH_2$; —$NH_2$; —CHO; and —COOH; $Z^1$ and $Z^2$, independently, are selected from —$NR^7R^8$; and $R^7$, $R^8$, and $R^9$, independently, are selected from H, $C_1$-$C_6$ alkyl, $C_2$-$C_6$ alkenyl, and $C_2$-$C_6$ alkynyl. In one embodiment, $Z^1$ and $Z^2$ are independently selected from —$NHCH(CH_3)_2$ and —$NHCH_2CH_3$.

In one embodiment, the compound is a compound of formula (2) in which $R^1$, $R^2$, $R^3$, $R^4$, $R^5$, and $R^6$, independently, are H; $Z^1$ and $Z^2$, independently, are selected from —$NR^7R^8$; and $R^7$, $R^8$, and $R^9$, independently, are selected from H, and $C_1$-$C_4$ alkyl. In one embodiment, $Z^1$ and $Z^2$ are independently selected from —$NHCH(CH_3)_2$ and —$NHCH_2CH_3$.

A second aspect of the invention provides a compound of Formula (A) or Formula (B):

Formula (A)

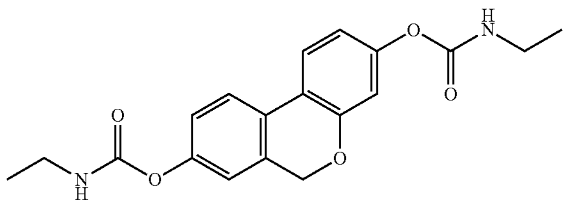

Formula (B)

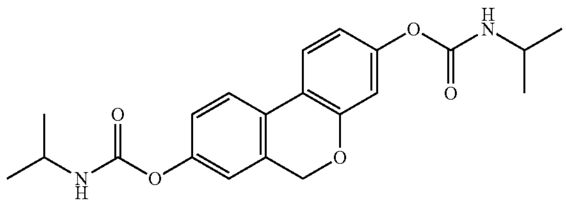

In embodiment, the compound is a compound of Formula (A).

In embodiment, the compound is a compound of Formula (B).

A third aspect of the invention provides pharmaceutically acceptable salt, solvate or prodrug of the compound of the first or second aspect of the invention.

The compounds of any Formula described herein include the compounds themselves, as well as their salts, and their solvates, if applicable. A salt, for example, can be formed between an anion and a positively charged group (e.g., amino) on a substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on a substituted benzene compound. Suitable cations include sodium ion, potassium ion, magnesium ion, calcium ion, and an ammonium cation such as tetramethylammonium ion. The substituted benzene compounds also include those salts containing quaternary nitrogen atoms.

For the purposes of this invention, a "salt" of a compound of the present invention includes one formed between a protic acid functionality (such as a carboxylic acid or alkyl sulphonic groups) of a compound of the present invention and a suitable cation. Examples of suitable salts include but are not limited to mesylate and tosylate. Suitable cations include, but are not limited to lithium, sodium, potassium, magnesium, calcium and ammonium. The salt may be a mono-, di-, tri- or multi-salt. Preferably the salt is a mono- or di-lithium, sodium, potassium, magnesium, calcium or ammonium salt. More preferably the salt is a mono- or di-sodium salt or a mono- or di-potassium salt.

Preferably any salt is a pharmaceutically acceptable non-toxic salt. However, in addition to pharmaceutically acceptable salts, other salts are included in the present invention, since they have potential to serve as intermediates in the purification or preparation of other, for example, pharmaceutically acceptable salts, or are useful for identification, characterisation or purification of the free acid or base.

The compounds and/or salts of the present invention may be anhydrous or in the form of a hydrate (e.g. a hemihydrate, monohydrate, dihydrate or trihydrate) or other solvate. Such solvates may be formed with common organic solvents, including but not limited to, alcoholic solvents e.g. methanol, ethanol or isopropanol.

In some embodiments of the present invention, therapeutically inactive prodrugs are provided. Prodrugs are compounds which, when administered to a subject such as a human, are converted in whole or in part to a compound of the invention. In most embodiments, the prodrugs are pharmacologically inert chemical derivatives that can be converted in vivo to the active drug molecules to exert a therapeutic effect. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include, but are not limited to, compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound. The present invention also encompasses salts and solvates of such prodrugs as described above.

The compounds, multi-salts, solvates and prodrugs of the present invention may contain at least one chiral centre. The compounds, salts, solvates and prodrugs may therefore exist in at least two isomeric forms. The present invention encompasses racemic mixtures of the compounds, salts, solvates and prodrugs of the present invention as well as enantiomerically enriched and substantially enantiomerically pure isomers. For the purposes of this invention, a "substantially enantiomerically pure" isomer of a compound comprises less than 5% of other isomers of the same compound, more typically less than 2%, and most typically less than 0.5% by weight.

The compounds, salts, solvates and prodrugs of the present invention may contain any stable isotope including, but not limited to $^{12}C$, $^{13}C$, $^{1}H$, $^{2}H$ (D), $^{14}N$, $^{15}N$, $^{16}O$, $^{17}O$, $^{18}O$, $^{19}F$ and $^{127}I$, and any radioisotope including, but not limited to $^{11}C$, $^{14}C$, $^{3}H$ (T), $^{13}N$, $^{15}O$, $^{18}F$, $^{123}I$, $^{124}I$, $^{125}I$ and $^{131}I$.

The compounds, salts, solvates and prodrugs of the present invention may be in any polymorphic or amorphous form.

A fourth aspect of the invention provides a pharmaceutical composition comprising a compound of the first or second aspect of the invention, or a pharmaceutically acceptable salt, solvate or prodrug of the third aspect of the invention, and a pharmaceutically acceptable excipient.

Conventional procedures for the selection and preparation of suitable pharmaceutical formulations are described in, for example, "Aulton's Pharmaceutics—The Design and Manufacture of Medicines", M. E. Aulton and K. M. G. Taylor, Churchill Livingstone Elsevier, $4^{th}$ Ed., 2013.

Pharmaceutically acceptable excipients including adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinylpyrrolidone, cellulose-based substances, polyethylene glycol, sodium carboxymethylcellulose, polyacrylates, waxes, polyethylene-polyoxypropylene-block polymers, polyethylene glycol and wool fat.

A fifth aspect of the invention provides a compound of the first or second aspect of the invention, or a pharmaceutically acceptable salt, solvate or prodrug of the third aspect of the invention, or a pharmaceutical composition of the fourth aspect of the invention, for use in medicine, and/or for use in the treatment or prevention of a disease, disorder or condition.

In one embodiment, the disease, disorder or condition is selected from the group consisting of mitochondrial diseases (including for example poor growth, loss of muscle coordination, muscle weakness, visual problems, hearing problems, heart disease, liver disease, kidney disease, gastrointestinal disorders, respiratory disorders, neurological problems, metabolic syndrome, cardiovascular disease, sarcopenia, muscle degenerative disease, liver diseases, nonalcoholic fatty liver disease (NAFLD), nonalcoholic steatohepatitis (NASH), ischemia/reperfusion injury, inflammatory bowel disease, Crohn's disease, type II diabetes mellitus, hyperlipidemia, neurodegenerative disease, Alzheimer's disease, Parkinson's disease, Huntington's disease, anxiety disorder, cancer.

A sixth aspect of the invention provides the use of a compound of the first or second aspect, a pharmaceutically effective salt, solvate or prodrug of the third aspect, or a pharmaceutical composition according to the fourth aspect, in the manufacture of a medicament for the treatment or prevention of a disease, disorder or condition. Typically the treatment or prevention comprises the administration of the compound, salt, solvate, prodrug or pharmaceutical composition to a subject. In one embodiment, the disease, disorder or condition is selected from the group consisting of mitochondrial diseases (including for example poor growth, loss of muscle coordination, muscle weakness, visual problems, hearing problems, heart disease, liver disease, kidney disease, gastrointestinal disorders, respiratory disorders, neurological problems, metabolic syndrome, cardiovascular disease, sarcopenia, muscle degenerative disease, liver diseases, nonalcoholic fatty liver disease (NAFLD), nonalcoholic steatohepatitis (NASH), ischemia/reperfusion injury, inflammatory bowel disease, Crohn's disease, type II diabetes mellitus, hyperlipidemia, neurodegenerative disease, Alzheimer's disease, Parkinson's disease, Huntington's disease, anxiety disorder, cancer.

A seventh aspect of the invention provides a method of treatment or prevention of a disease, disorder or condition, the method comprising the step of administering an effective amount of a compound of the first or second aspect, or a pharmaceutically acceptable salt, solvate or prodrug of the third aspect, or a pharmaceutical composition of the fourth aspect, to thereby treat or prevent the disease, disorder or condition. Typically the administration is to a subject in need thereof. In one embodiment, the disease, disorder or condition is selected from the group consisting of mitochondrial diseases (including for example poor growth, loss of muscle coordination, muscle weakness, visual problems, hearing problems, heart disease, liver disease, kidney disease, gastrointestinal disorders, respiratory disorders, neurological problems, metabolic syndrome, cardiovascular disease, sarcopenia, muscle degenerative disease, liver diseases, nonalcoholic fatty liver disease (NAFLD), nonalcoholic steatohepatitis (NASH), ischemia/reperfusion injury, inflammatory bowel disease, Crohn's disease, type II diabetes mellitus, hyperlipidemia, neurodegenerative disease, Alzheimer's disease, Parkinson's disease, Huntington's disease, anxiety disorder, cancer.

In general embodiments, the disease, disorder or condition may be a disease, disorder or condition of the immune system, the cardiovascular system, the endocrine system, the gastrointestinal tract, the renal system, the hepatic system, the metabolic system, the respiratory system, the central nervous system, and/or may be caused by or associated with a pathogen.

It will be appreciated that these general embodiments defined according to broad categories of diseases, disorders and conditions are not mutually exclusive. In this regard any particular disease, disorder or condition may be categorized according to more than one of the above general embodiments. A non-limiting example is type I diabetes which is an autoimmune disease and a disease of the endocrine system.

In one embodiment of the fifth, sixth, or seventh aspect of the present invention, the disease, disorder or condition is selected from but not limited to: metabolic stress, cardiovascular disease, endothelial cell dysfunction, sarcopenia, muscle degenerative disease, Duchenne muscular dystrophy, alcoholic liver disease, nonalcoholic fatty liver disease, drug-induced liver injury, a 1-antitrypsin deficiency, ischemia/reperfusion injury, inflammation, aging of the skin, inflammatory bowel disease, Crohn's disease, obesity, metabolic syndrome, type II diabetes mellitus, hyperlipidemia, osteoarthritis, neurodegenerative disease, Alzheimer's disease, Huntington's disease, Parkinson's disease, amyotrophic lateral sclerosis, age-related macular degeneration, mitochondrial diseases (including for example poor growth, loss of muscle coordination, muscle weakness, visual problems, hearing problems, heart disease, liver disease, kidney disease, gastrointestinal disorders, respiratory disorders, neurological problems, autonomic dysfunction sometimes learning disabilities, and dementia as a result of mitochondrial disease), muscle diseases; sporadic inclusion body myositis (sIBM), cancer, cognitive disorder, stress, and mood disorder.

In one embodiment, the disease, disorder or condition is selected from but not limited to: muscle degenerative disease, cardiovascular disease, sarcopenia, nonalcoholic fatty liver disease (NAFLD), ischemia/reperfusion injury, inflammatory bowel disease, Crohn's disease, type II diabetes mellitus, hyperlipidemia, neurodegenerative disease, Alzheimer's disease, Parkinson's disease, Huntington's disease, anxiety disorder, cancer.

In one embodiment, the disease, disorder or condition is a neurodegenerative disorder, such as Alzheimer's disease, Parkinson's disease, or ischemia.

Unless stated otherwise, in any aspect of the invention, the subject may be any human or other animal. Typically, the subject is a mammal, more typically a human or a domesticated mammal such as a cow, pig, lamb, goat, horse, cat, dog, etc. Most typically, the subject is a human.

Any of the medicaments employed in the present invention can be administered by oral, parental (including intravenous, subcutaneous, intramuscular, intradermal, intratracheal, intraperitoneal, intraarticular, intracranial and epidural), airway (aerosol), rectal, vaginal or topical (including transdermal, buccal, mucosal and sublingual) administration.

Typically, the mode of administration selected is that most appropriate to the disorder or disease to be treated or prevented.

For oral administration, the compounds, multi-salts, solvates or prodrugs of the present invention will generally be provided in the form of tablets, capsules, hard or soft gelatine capsules, caplets, troches or lozenges, as a powder or granules, or as an aqueous solution, suspension or dispersion.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose. Corn starch and alginic acid are suitable disintegrating agents. Binding agents may include starch and gelatine. The lubricating agent, if present, may be magnesium stearate, stearic acid or tale. If desired, the tablets may be coated with a material, such as glyceryl monostearate or glyceryl distearate, to delay absorption in the gastrointestinal tract. Tablets may also be effervescent and/or dissolving tablets. Capsules for oral use include hard gelatine capsules in which the active ingredient is mixed with a solid diluent, and soft gelatine capsules wherein the active ingredient is mixed with water or an oil such as peanut oil, liquid paraffin or olive oil.

Powders or granules for oral use may be provided in sachets or tubs. Aqueous solutions, suspensions or dispersions may be prepared by the addition of water to powders, granules or tablets.

Any form suitable for oral administration may optionally include sweetening agents such as sugar, flavouring agents, colouring agents and/or preservatives.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For parenteral use, the compounds, multi-salts, solvates or prodrugs of the present invention will generally be provided in a sterile aqueous solution or suspension, buffered to an appropriate pH and isotonicity. Suitable aqueous vehicles include Ringer's solution and isotonic sodium chloride or glucose. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate. The compounds of the invention may also be presented as liposome formulations.

For transdermal and other topical administration, the compounds, multi-salts, solvates or prodrugs of the invention will generally be provided in the form of ointments, cataplasms (poultices), pastes, powders, dressings, creams, plasters or patches.

Suitable suspensions and solutions can be used in inhalers for airway (aerosol) administration.

The dose of the compounds, multi-salts, solvates or prodrugs of the present invention will, of course, vary with the disorder or disease to be treated or prevented. In general, a suitable dose will be in the range of 0.01 to 500 mg per kilogram body weight of the recipient per day. The desired dose may be presented at an appropriate interval such as once every other day, once a day, twice a day, three times a day or four times a day. The desired dose may be administered in unit dosage form, for example, containing 1 mg to 50 g of active ingredient per unit dosage form.

For the avoidance of doubt, insofar as is practicable any embodiment of a given aspect of the present invention may occur in combination with any other embodiment of the same aspect of the present invention. In addition, insofar as is practicable it is to be understood that any preferred, typical or optional embodiment of any aspect of the present invention should also be considered as a preferred, typical or optional embodiment of any other aspect of the present invention.

Examples—Compound Synthesis

Compounds of the invention are synthesised employing a route of synthesis shown below. The general route of synthesis is illustrated below by reference to the synthesis of a specific compound. However, this is merely illustrative of a more general synthesis that can be employed to synthesise all compounds of the invention.

Route of synthesis:

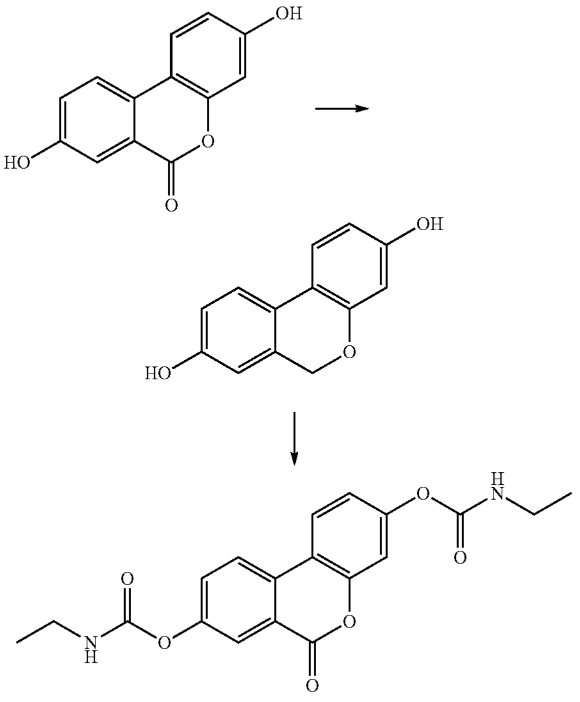

Synthesis of SND305 & SND306

Sodium borohydride (0.165 g, 4.38 mmol) was added to dry THF (10 ml), and the mixture was cooled to 10° C. before borontrifluoride etherate (0.80 g, 5.7 mmol) was added drop wise over a period of 1 h. Then 3,8-dihydroxy-6H-benzo[c]chromen-6-one (0.5 g, 2.19 mmol) in THF (5 ml) was added over a period of 10 min. The mixture was allowed to stir for 5 h at 50° C. The completion of reaction was monitored by thin layer chromatography (TLC). The reaction was quenched with methanol. 3 N aqueous HCl solution (10 ml) was added, and the mixture was gently heated to 50° C. for 30 min. The reaction mixture was adjusted to neutral with 10% NaOH solution, and the volatiles were evaporated under reduced pressure. The crude product was purified by column chromatography using 50% ethyl acetate in hexane with 60-120 mesh silica gel to get pure 6H-benzo[c]chromene-3,8-diol product.

M+=215.2.

NMR (DMSO-d6): 9.49 (2H, s), 7.51-7.50 (1H, d, J 6.6 Hz), 7.48-7.47 (1H, d, J6.6 Hz), 6.75-6.73 (1H, m), 6.61 (1H, s), 6.48-6.46.

Synthesis Example 1: Synthesis of SND305 & SND306

The above 6H-benzo[c]chromene-3,8-diol product (10 mM) was dissolved in 10 ml acetonitrile then 50 mM anhydrous potassium carbonate were added to the solution. After 30 min of stirring at 5-10 deg C. 12 mM of the respective alkyl isocyanate was added slowly under stirring and the resulting suspension was warmed up at 70° C. for 6 hours. The reaction mixture was filtered and the filtrate and washings concentrated in vacuo. Preparative HPLC yielded pure white powder.

H1—NMR and LCMS clearly support the structures.

SND 305: R=C2H5, SND 306: R=CH(CH3)2

Yield: SND 305=81%; SND 306=81%.

Examples—Compounds

The following compounds have been prepared using the same synthesis.

SND305

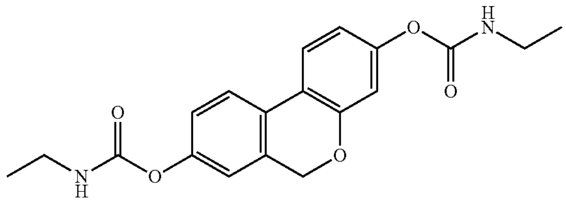

SND306

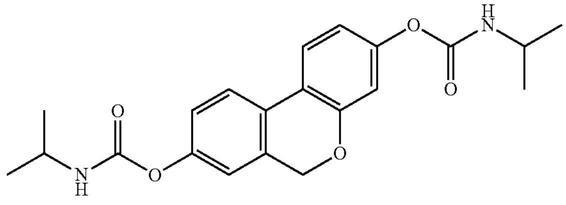

Examples—Biological Studies

Example 1: Effect of Cpd1 on *C. elegans* Life Span

It has been recently shown that urolithin A (UA) is a first-in-class natural compound that induces mitophagy both in vitro and in vivo following oral consumption; see Ryu et al, 2016, "Urolithin A induces mitophagy and prolongs lifespan in *C. elegans* and increases muscle function in rodents", Nature Medicine, vol. 22, pages 879-888. In *C. elegans*, UA prevented the accumulation of dysfunctional mitochondria with age and extended lifespan.

Age-dependent accumulation of mitochondrial abnormalities and mutant proteins lead to both structural and functional changes in neuronal function and to cell death. Thus, the use of a whole organism such as *C. elegans* in an ageing setting serves as a model for potential neurodegenerative diseases [Knott, A., Perkins, G., Schwarzenbacher, R. et al. Mitochondrial fragmentation in neurodegeneration. *Nat Rev Neurosci* 9, 505-518 (2008)], muscle function [Alway S E, Mohamed J S, Myers M J. Mitochondria Initiate and Regulate Sarcopenia. *Exerc Sport Sci Rev.* 2017; 45(2):58-69] as well as other degenerative conditions [Shah S J, Paine J G, Perez C, Ullah G. Mitochondrial fragmentation and network architecture in degenerative diseases. *PLoS One.* 2019; 14(9]

Experimental Method:

Worm Maintenance and Media

To prevent chemical modification or metabolism of the test article by the food bacteria, worms were fed on a lawn of UV-killed bacteria (UV-i bacteria). An overnight culture of *E. coli* strain WP-2 was pelleted, washed, filtered, and irradiated. A suspension of UV-i bacteria was spotted on NGM agar containing Streptomycin to inhibit the growth of contaminating bacteria. The quantity and distribution of food bacteria were calibrated to ensure adequate access to food for the duration of assay while maintaining visibility of the worms.

Solubilization and Delivery

Test compounds were soluble in 100% DMSO. The compounds were dissolved in a working solution and then combined directly with the food bacteria before seeding on agar plates. The food spots are dried slowly, allowing the compound to diffuse into the food bacteria and the agar for at least 24 hours before worms were introduced.

Automated Lifespan Machine (ALM)

The ALM used by InVivoBiosystems is based on the *Caenorhabditis elegans* lifespan machine published by Stroustrup et. Al [Stroustrup, N. et al. The *Caenorhabditis elegans* Lifespan Machine. *Nat Methods* 10, 665-670 (2013)], with proprietary modifications to improve temperature stability and image acquisition. The scanner unit consisted of a modified EPSON V850 and images were processed and analyzed using the ALM software. The machine time-of-death calls are trained and validated using the "storyboarding" feature of the ALM software.

Lifespan Assay

The lifespan assay was designed and performed according to published and validated methods [Amrit, F. R. G., Ratnappan, R., Keith, S. A. & Ghazi, A. The *C. elegans* lifespan assay toolkit. *Methods* 68, 465-475 (2014).] using a modified version of the Automated Lifespan Machine 7.

The lifespan assay was initiated by expanding all replicate groups to more than 1000 worms, then synchronizing by bleaching and allowing larval worms to hatch and arrest. To suppress progeny, worms were transferred to media containing 5-Fluorodeoxyuridine (FUdR) within 54-60 hours post-plating. Worms were inspected 24 and 48 hours after this transfer to confirm infertility. Finally, the worms were inspected for general health and morphology before transferring to scanner plates. The scanner plates were transferred to scanners for automated imaging on day 3 of adulthood.

Plates were immobilized inverted on the bed of an Automated Lifespan Machine which scanned two images per hour of the plates continuously for the next 40 days.

Survival Analysis

Time of death calls exported from the ALM software was analyzed and plotted using the Lifelines software package developed by Cam Davidson-Pilon et. al [Davidson-Pilon, C et. al. Lifelines survival analysis package. CamDavidson-Pilon/lifelines: vo. 25-9.]. Additional analysis was performed using the OASIS2 analysis software6.

Worm movement was tracked from the images acquired by the ALM during the lifespan assay. Worm size and movement features were extracted and analyzed using custom software.

Results

To determine the optimal dose for treatment in the lifespan assay, the compounds were tested for acute toxicity in adult worms by simulating the actual conditions of the lifespan assay. Worms were treated with either vehicle control or compound at doses spanning a range from 10 μM to 100 μM on media identical to what would be used in the lifespan experiment. High-resolution imaging and automated detection are used to precisely measure the growth rate of animals from hatching to the first day of adulthood (total of 4 days).

For all compounds, no significant adverse effects were detected in this range, therefore the concentration of 50 μM was chosen for the lifespan assays.

Treatment with either SND305 or SND306, increased the life span with statistical significance as shown in Table 1 and Table 2.

The increase in median lifespan for these compounds exceeded the 50 th percentile of life-extending compounds tested to date on this platform. By convention, the "maximum lifespan" is typically the 95th percentile of lifespans recorded. Treatment with any of the compounds produced a modest increase in maximum lifespan whereas the positive control, Rapamycin did not increase maximum lifespan.

TABLE 1

Life span assay summary. Lifespan is counted with day 1 set at day 1 of adulthood. No death times are recorded until worms are placed on the scanner on day 3 of adulthood, so earlier deaths are excluded from calculations of mean and median.

| Treatment | Vehicle | SND305 | SND306 | Rapamycin |
|---|---|---|---|---|
| Median life span (Days) | 25.1 | 26.7 | 26.6 | 26.5 |
| Median 95% CI | 24.7-25.5 | 25.9-28.5 | 26.4-26.8 | 26.0-27.2 |
| Mean life span (Days) | 24.1 | 26.0 | 25.8 | 26.2 |
| Mean 95% CI | 23.7-24.5 | 24.7-27.3 | 25.4-26.2 | 25.6-26.8 |
| Max life span (Days) | 33.0 | 34.9 | 34.6 | 33.0 |

Median lifespan is equal to the time at which 50% of the worms have died.
Mean lifespan is calculated from the area under the survival curve.
Maximum lifespan is equal to 95th percentile of lifespans in each group.
CI: Confidence Interval.
Vehicle control DMSO 0.1%; the concentration of all compounds 50 μM.

TABLE 2

Pairwise statistical analysis of survival curves. The Mantel-Cox log-rank test is a non-parametric test that compares two survival functions across the duration of the lifespan.

| Curve comparison | Test statistic (X2) | Log-rank test P-value |
|---|---|---|
| SND305 v.s. vehicle control | 23.83 | 0.0000042 **** |
| SND306 v.s. vehicle control | 25.84 | 0.0000015 **** |
| Rapamycin v.s. vehicle control | 20.46 | 0.000024 **** |

P-value is corrected for multiple comparisons (Bonferroni correction). Numbers and asterisks represent P-value and significance, respectively.

Example 2: Effect of SND Derivatives on *C. elegans* Gene Expression

To identify potential mechanisms of action through which SND305 and SND306 could affect aging, global gene expression was analyzed by mRNA sequencing (RNA-Seq). Worms were treated on the same media and conditions as the lifespan assay, then young worms were harvested at adult day 3 and aged worms harvested at adult day 10. Three replicates of treated samples were analyzed.

Experimental Method

Whole Transcriptome Analysis

More than 300 day 1 adult worms per replicate were harvested, cleaned by filtration, and frozen at −80° in Trizol. To extract RNA, samples were thawed, vigorously vortexed, and processed using the Direct-zol RNA Miniprep Kit (Zymo Research). All samples exceeded the threshold for RNA quantity and quality.

The total RNA was then enriched for poly-mRNA using oligo(dT) paramagnetic beads. DNA libraries were then constructed from this input mRNA using the NEBNext Ultra™ II RNA Library Prep Kit. This created a ready-to-sequence dsDNA library that retained the strand-specific information in the original mRNA. These libraries were then further tested by the Qubit for concentration and the Agilent 2100 for library size distribution and quality. In order to properly pool the libraries and load them onto sequencing lanes to ensure the correct number of reads per sample, an even more precise quantification of the library was done via qPCR, and the samples were loaded onto the NovaSeq 6000 platform for a paired-end sequencing run of 150 bp for each end (PE150). The loading concentrations were designed to obtain at least 6.0 Gb (which is the number of billion bases of raw data, determined by the number of reads multiplied by the length of each read).

The raw data set was analyzed for

1. The distribution of base quality along the length of the sequencing read
2. The distribution of error rate along the length of the sequencing read
3. The distribution of A/T/G/C bases along the length of the sequencing read
4. The distribution of raw data filtering results based on the following three criteria:
   a. Removing reads containing adapter sequence
   b. Removing reads with N>10% (where N means "base cannot be determined")
   c. Removing reads with a low quality (Qscore<=5) for 50% or more of its total bases Results Multidimensional scaling makes it possible to see strong patterns in large, complex data sets by reducing the data to two or three dimensions. When the data is plotted along these few dimensions, the samples form clustered based on their overall similarity to one another. The distance between samples is calculated based on the Biological Coefficient of Variation (BCV). Greater differences were observed between all conditions at Day 10 than at Day 3. To identify genes that are differentially expressed upon treatment with SND305 and SND306, the gene counts for each of the treated samples were compared against the control. The various comparisons groups used are shown in Table 3.

TABLE 3

Comparison groups for differential gene expression

| Group | Experiment | Control |
|---|---|---|
| 1 | SND305 day 3 | Vehicle day 3 |
| 2 | SND305 day 10 | Vehicle day 10 |
| 3 | SND306 day 3 | Vehicle day 3 |
| 4 | SND306 day 10 | Vehicle day 10 |

The volcano plots in FIG. 1 show the distribution of genes for each condition with a P-value<0.05 and a fold change >2.0. Each of these treatments induced only a small number of highly significant changes in gene expression at Day 3, consistent with the observations from the multidimensional scaling (MDS) plots. The SND305 treatment did indicate 3 upregulated genes, irg-4, cpr-1, and dod-21. The cpr-1 has been directly implicated in worm longevity [Murphy C T, McCarroll S A, Bargmann C I, Fraser A, Kamath R S, Ahringer J, Li H, Kenyon C. Genes that act downstream of DAF-16 to influence the lifespan of *Caenorhabditis elegans*. Nature. 2003 Jul. 17; 424(6946):277-83], whereas irg-4, and dod-21 are frequently observed under conditions of life-extension (InVivo Biosystems). At Day 10, the SND306 group showed a large number of DEGs above threshold whereas the SND305 group showed very few. A large number of genes encode proteins related to the structure or biosynthesis of collagen, which tend to form a large co-regulated cluster. It is interesting that the overall response at Day 10 for SND306 is significantly different from SND305 given the similarities in the lifespan and Day 3 gene expression.

Gene Ontology (GO) Term Enrichment Analysis

GO enrichment analysis is a common approach that identifies functional groups form lists of differentially expressed genes. Genes are annotated based on functional categories (gene ontologies) that are further categorized by biological process (BP), molecular function (MF), or cellular compartment (CC). A comparison is made between the likelihood of seeing genes in that category (ontology) being enriched or depleted in the list of DEGs when compared to a random selection of genes. This approach reveals patterns of interactions between many DEGs. GO terms are overlapping and nested by design, therefore Table 4 shows a consolidated summary of the GO terms results. The most salient result is that for both young and aged worms, SND305 and SND306 showed very similar patterns of GO enrichment.

At Day 3, these two groups showed enrichment of genes involved with cuticle structure (collagens), immune response. At Day 10, both the SND305 and SND306 showed an enrichment in genes involved with axon development and regeneration (Table 4).

TABLE 4

| Summary of GO enrichment analysis | | | |
|---|---|---|---|
| Compound | Day | Up/ Down | Noteable categories enriched or depleted (condensed from tables in Appendix) |
| SND305 | 3 | Up | extracellular region, immune response, response to other organism, lysosome |
| | | Down | None detected. |
| | 10 | Up | Nervous system development, neurogenesis, regulation of gene expression |
| | | Down | extracellular region, immune response, response to other organism |
| SND306 | 3 | Up | structural constituent of cuticle (e.g. collagen), immune response, lipid biosynthesis |
| | | Down | hydrolase activity |
| | 10 | Up | nervous system development, neurogenesis, regulation of gene expression |
| | | Down | extracellular region, immune response, response to other organism |

Pathway Mapping

In order to identify which cellular pathways were most likely modulated by treatment with SND305 and SND306 and gain insight into how these pathways might contribute to mechanism of action (MoA), the genes differentially expressed after SND305 and SND306 treatment were mapped to core established longevity pathways from the literature. The mapping was then expanded to intersecting and supporting pathways. This placed the transcriptomic data within the context of well-characterized biological pathways, particularly several related to longevity.

Figure 2:
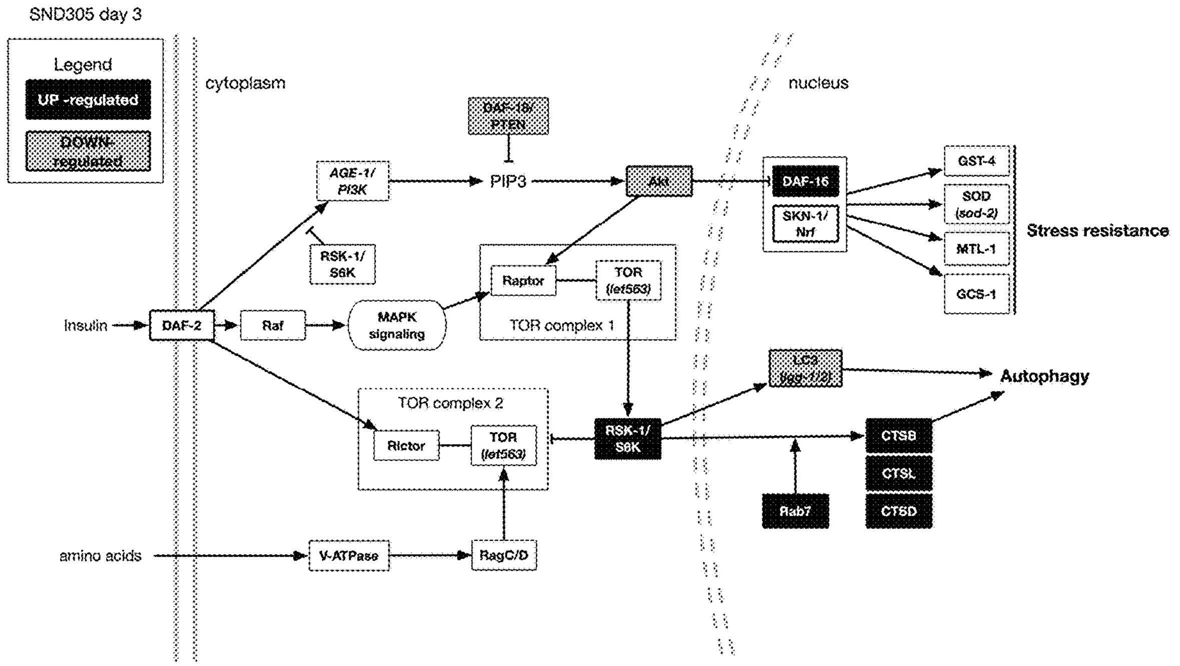
FIG. 2 shows the connectivity of known aging-related pathways represented by genes differentially regulated under SND305 treatment in young (Day 3) worms. Shading indicates the change of expression, up-(black) or down-(grey). Uncolored objects indicate components that were not detected in the data. Fold changes, weighted by the p-value, were as follows: CTSB, >5 fold up-; CTSL, 2 to 3 fold up-; CTSD, 2 to 3 fold up-; Rab7, 2 to 3 fold up-; RSK-1/S6K, 2 to 3 fold up-; DAF-16, 2 to 3 fold up-; DAF-18/PTEN, 1 to 2 fold down-; Akt, 1 to 2 fold down-; LC3 (lgg-1/2), 1 to 2 fold down-.
Figure 3:
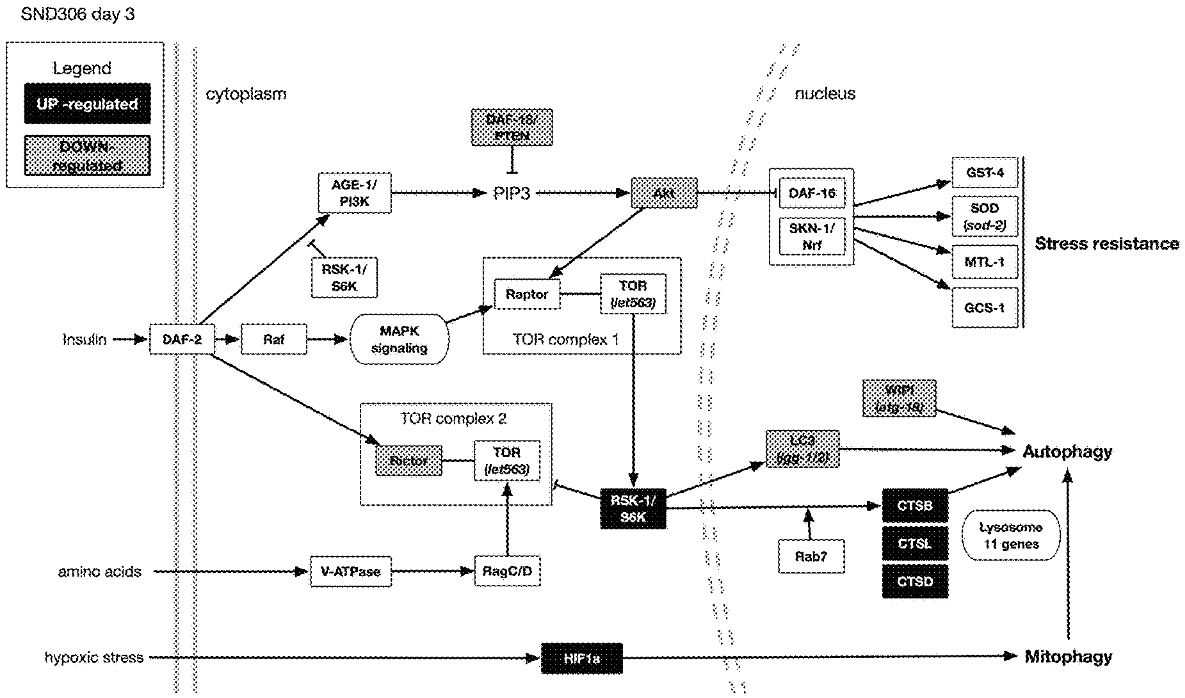
FIG. 3 shows the connectivity of known aging-related pathways represented by genes differentially regulated under SND306 treatment in young (Day 3) worms. Shading indicates the change of expression, up-(black) or down-(grey). Uncolored objects indicate components that were not detected in the data. Fold changes, weighted by the p-value, were as follows: CTSB, 2 to 3 fold up-; CTSL, 2 to 3 fold up-; CTSD, 2 to 3 fold up-; HIF1a, 2 to 3 fold up-; RSK-1/S6K, 2 to 3 fold up-; DAF-18/PTEN, 1 to 2 fold down-; Akt, 1 to 2 fold down-; LC3 (lgg-1/2), 1 to 2 fold down-; WIPI (atg-18), 1 to 2 fold down-; Rictor, 1 to 2 fold down-.

Worms treated with SND305 and SND306 showed changes in expression of several key members of canonical longevity pathways at day 3 (FIGS. 2 and 3). The Insulin Signaling (IIS) Pathway is most commonly associated with lifespan in part due to its role in caloric restriction. In SND305- and SND306-treated worms, there is a slight modulation of some of the pathway components, daf-18, akt-1, and daf-16, but not a strong signal from the downstream targets of the pathway (FIGS. 2 and 3).

Figure 4:
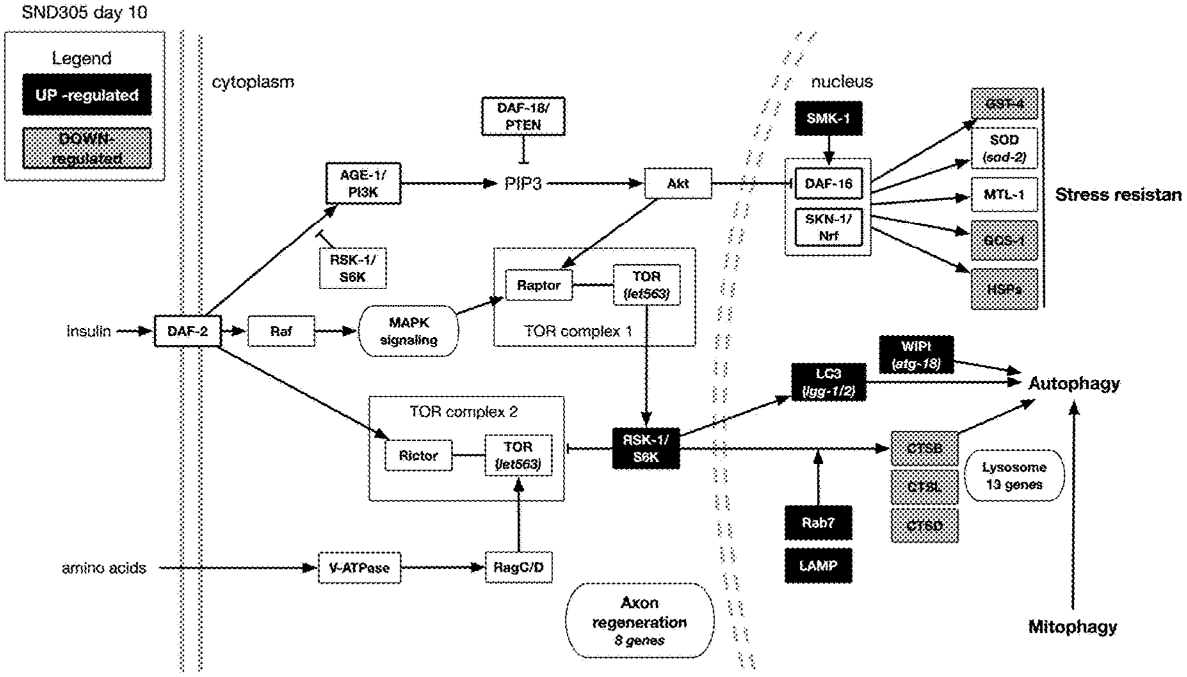
FIG. 4 shows the connectivity of known aging-related pathways represented by genes differentially regulated under SND305 treatment in aged (Day 10) worms. Shading indicates the change of expression, up-(black) or down-(grey). Uncolored objects indicate 20 components that were not detected in the data. Fold changes, weighted by the p-value, were as follows: SMK-1, 2 to 3 fold up-; WIPI (atg-18), 2 to 3 fold up-; LC3 (lgg-1/2), 2 to 3 fold up-; Rab7, 2 to 3 fold up-; RSK-1/S6K, 2 to 3 fold up-; LAMP, 2 to 3 fold up-; GST-4, 1 to 2 fold down-; GCS-1, 1 to 2 fold down-; HSPs, 1 to 2 fold down-; CTSB, 1 to 2 fold down-; CTSL, 1 to 2 fold down-; CTSD, 1 to 2 fold down-.
Figure 5:
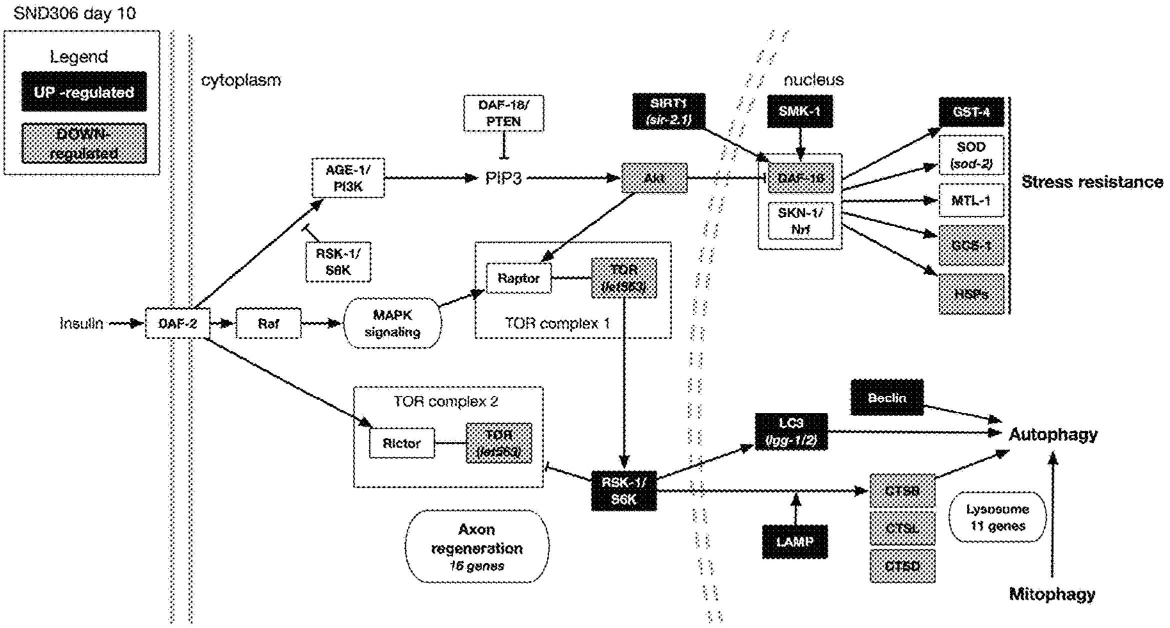
FIG. 5 shows the connectivity of known aging-related pathways represented by genes differentially regulated under SND306 treatment in aged (Day 10) worms. Shading indicates the change of expression, up-(black) or down-(grey). Uncolored objects indicate components that were not detected in the data. Fold changes, weighted by the p-value, were as follows: LAMP, >5 fold up-; SMK-1, 2 to 3 fold up-; SIRT1 (sir-2.1), 2 to 3 fold up-; GST-4, 2 to 3 fold up-; Beclin, 2 to 3 fold up-; LC3 (lgg-1/2), 2 to 3 fold up-; RSK-1/S6K, 2 to 3 fold up-; CTSB, >5 fold down-; CTSD, >5 fold down-; CTSL, 2 to 3 fold down-; Akt, 1 to 2 fold down-; GCS-1, 1 to 2 fold down-; HSPs, 1 to 2 fold down-; DAF-16, 1 to 2 fold down-; TOR (let563), 1 to 2 fold down-.

Autophagy is another key longevity-associated pathway that is involved in cellular regeneration and homeostasis. Cathepsins are proteases involved in late critical steps of autophagy. In both the SND305 and SND306 groups, all three cathepsin orthologs, cpr-1, cpr-4, cpr-9 are upregulated, supporting a model in which these compounds are activating autophagy (FIGS. 2 and 3). At Day 10 there were a larger number of DEGs for all treatments, and the gene expression profiles had diverged further. The effects of SND305 and SND306, however, remained similar. Most notably, SND305 and SND306 groups showed upregulation of genes specifically involved in axon regeneration (FIGS. 4 and 5), as suggested by the GO enrichment analysis above.

Example 3. Age-Related Sarcopenia Model

*C. elegans* can function as a model for sarcopenia-related muscle degeneration due to the ability to directly visualize fluorescently-labelled (GFP) mitochondrial structure in the muscle, in a short-term aging study [Gaffney C J, Pollard A, Barratt T F, Constantin-Teodosiu D, Greenhaff P L, Szewczyk N J. Greater loss of mitochondrial function with ageing is associated with earlier onset of sarcopenia in *C. elegans*. Aging (Albany NY). 2018; 10(11):3382-3396].

Sarcopenia is a type of muscle loss that occurs in most organisms concurrent with aging suggesting it is an evolutionarily conserved process. It is typically characterized by the degenerative loss of muscle mass and quality and decreased strength. Muscle mitochondrial dysfunction is observed at the onset of sarcopenia, followed by subsequent changes in sarcomere structure and ultimately movement decline.

Experimental Method:

*C. elegans* strain SD1347 confirmed to have nuclear and mitochondrial GFP labeling in muscle was obtained from the *Caenorhabditis* Genetic Center.

Synchronized worm populations were administered a single concentration of 50 μM SND compounds by exposure on NGM plates starting the day before adulthood. All plates contained 50 μM 5-Fluorodeoxyuridine (FUdR) to prevent progeny production. Animals were immobilized using NemaGel (InVivo Biosystems) and imaged within 1 hour. Worms were alive throughout imaging. For each worm imaged, one head and one tail image was collected from regions excluding the pharynx, vulva, and tip of the tail. For day 1, a single session imaged a minimum of 5 worms per condition.

For aged worms, two total biological replicates were collected, each with 5-6 worms imaged per condition. Images were obtained using a Nikon Eclipse Ti2 spinning disk confocal microscope. After processing, each image was scored blindly in replicate groups by six viewers.

Drug Formulation and Delivery

Stock solutions of SND compounds were prepared by dissolving to 50 mM in DMSO. Working solutions were prepared such that the final concentration of compound in the total volume of the solid media would be 50 μM, and the DMSO concentration would not exceed 0.1% (e.g. 10 μl in a 10 mL dish). The total volume of DMSO working stock was combined directly with food bacteria, incubated for 1 minute to adsorb/penetrate bacteria, then seeded on plates and dried immediately.

Microscopy

All slides were prepared immediately before imaging, and live worms were imaged within 1 hour of mounting. Worms were transferred by picking to a 10 μL cold M9 buffer on an adhesion-coated glass slide. 30 μL of a 30% pleuronic gel (NemaGel, InVivo Biosystems) was added to the M9 and compressed with a cold #1.5 coverglass. The slide was incubated for 2 minutes at 25° to harden the NemaGel, then imaged immediately. Images were acquired using a Nikon Eclipse Ti2 Spinning Disk Confocal Microscope with a 40× immersion objective. Laser intensity, exposure, and gain settings were maintained constant for all images collected. A head and tail image was collected from each worm from regions between and excluding the pharynx, tail tip, and vulva. Images were processed to create a maximum-intensity projection and noise was reduced by non-local mean denoising (Sci-kit image).

Manual Image Analysis

All images were blinded and delivered to viewers in a random order. Viewers were given a practice set of images before scoring and instructed to rate the mitochondrial fragmentation from 0 (completely intact) to 3 (completely disrupted). 0—Normal: Flat, corduroy-like striations, within cell: homogeneous, between cells: homogeneous; 1—Mild: Beads-on-a-string, within cell: mostly homogeneous, between cells: mostly homogeneous 2—Moderate: Globular beads, within cell: patches and gaps, between cells: heterogeneous 3—Severe: Most cells have completely disrupted structure.

For each image, the scores from each viewer were summed, then averaged within the samples. Statistical analysis was performed using ANOVA and Chi-square tests using Prism (GraphPad) software.

Results

Figure 6:
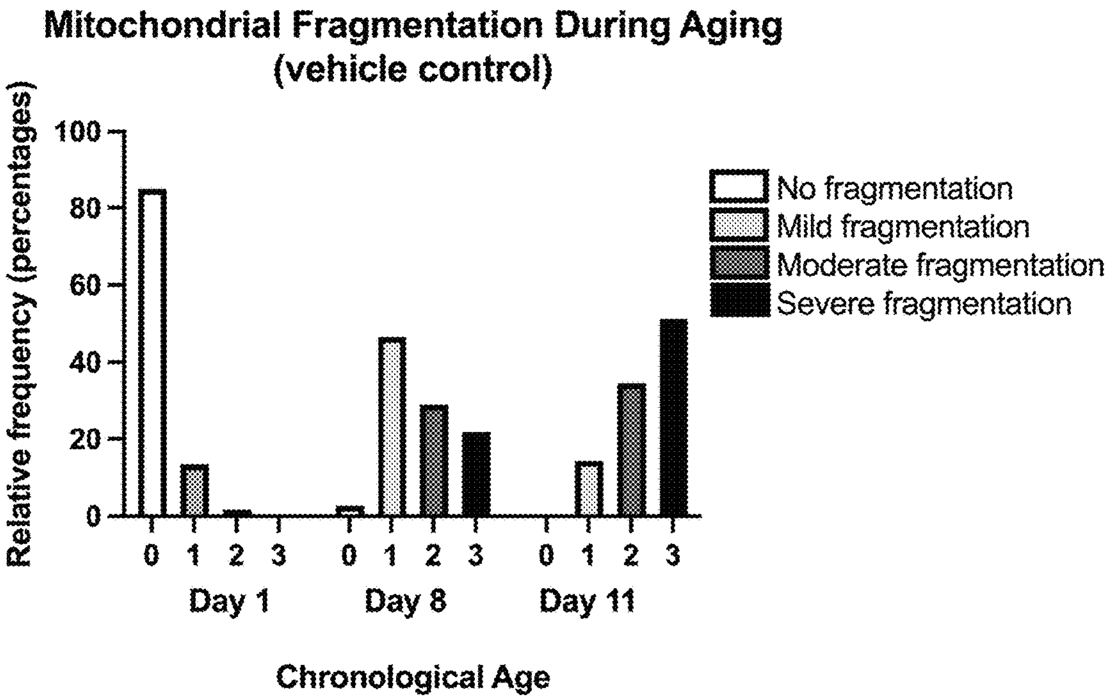
FIG. 6 shows the relative frequency of mitochondrial fragmentation scores of vehicle control at day 1, 8 and 11 representing the mitochondrial fragmentation during aging for a normal animal. Histograms where the bars represent the number of images assigned to each score bin.

At day 1, all conditions showed intact, striated patterns of mitochondrial fluorescence and no differences between conditions were visible by eye, denoted as "no fragmentation". At day 8, the vehicle control group presented mostly mild and moderate fragmentation. At day 11 more severe fragmentation in the vehicle control animals was observed as shown in FIG. 6.

Figure 7:
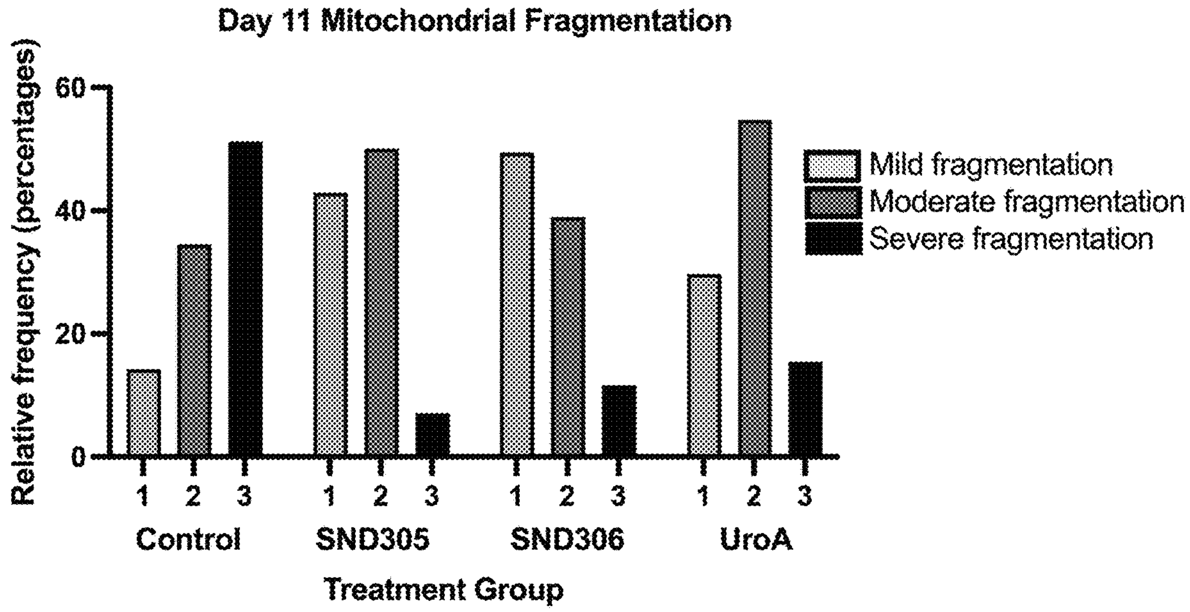
FIG. 7 shows the relative frequency of mitochondrial fragmentation scores for each treatment at day 11. Histogram bars represent the % of images assigned to each category from the total images captured.

Analysis of the day 11 images using the sum of the mitochondrial fragmentation scores per image showed each of the treated samples had highly significant less severe fragmentation than the control (FIG. 7). The statistical analysis indicated that the decrease in the relative frequency of fragmentation scores for all treatments vs control is highly significant $p<0.0001$.

Figure 8:
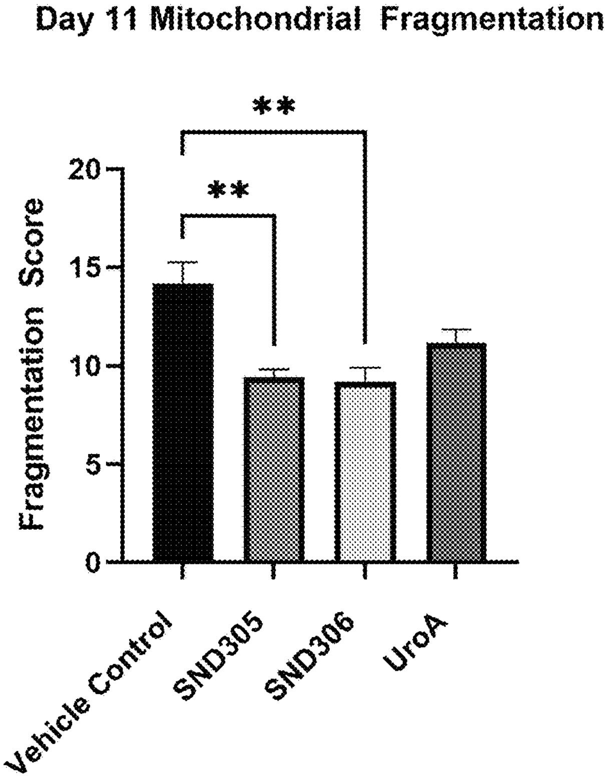
FIG. 8 shows differences between compound-treated worms and control. The bars represent mean sum of scores. Statistical analysis was performed using an ANOVA and multiple comparisons. $^{**}p<0.01$.

An analysis of the day 11 images using the sum of the mitochondrial fragmentation scores per image, showed significantly less fragmentation than the control for worms treated with SND305 and SND306 ($p<0.01$), but did not reach statistical significance for Urolithin A (FIG. 8).

Figure 9:
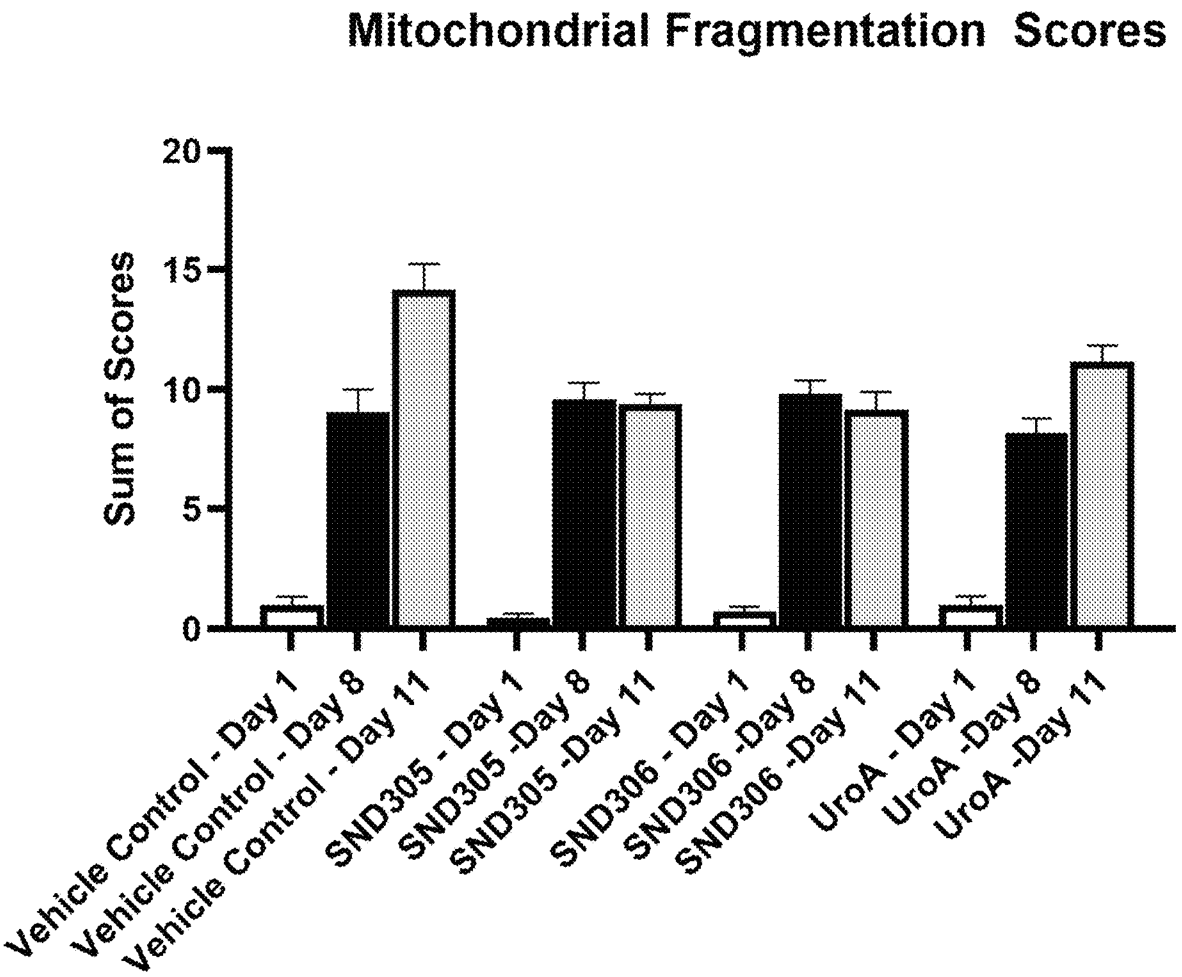
FIG. 9 shows the comparison mitochondrial fragmentation between days 1, day 8 and day 11. Bars represent manual scoring mean sum of scores.

Interestingly, the compound treated worms aged less than the control worms when the day 11 fragmentation scores were compared with the day 8 scores (FIG. 9). The treated worms showed no significant difference in scoring between day 8 and day 11, while the vehicle control showed a significant increase in mitochondrial fragmentation, denoted by an increase in the sum of scores (FIG. 9).

The invention claimed is:

1. A compound of formula (1), or a pharmaceutically acceptable salt or solvate thereof:

Formula (1)

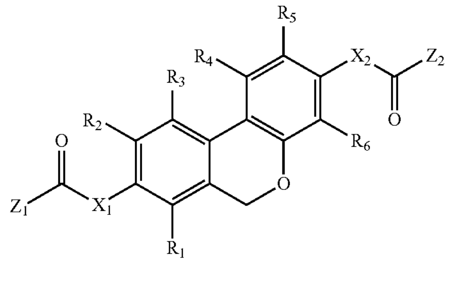

wherein:

$X_1$ and $X_2$ are —O—;

$R^1$, $R^2$, $R^3$, $R^4$, $R^5$, and $R^6$ are H; and $Z^1$ and $Z^2$ are —$NHR^8$, wherein $R^8$ is selected from $C_1$-$C_6$ alkyl or $C_3$-$C_7$ cyclic group;

wherein $R^8$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —$NO_2$, —C≡CH, —CHO, —$CON(CH_3)_2$ or oxo (═O) groups.

2. The compound as claimed in claim 1, wherein $R^8$ is $C_1$-$C_6$ alkyl.

3. The compound as claimed in claim 1, wherein $R^8$ is $C_{1-4}$ alkyl.

4. The compound as claimed in claim 1, wherein $R^8$ is ethyl, or propyl.

5. The compound as claimed in claim 1, wherein $Z^1$ and $Z^2$ are —$NHCH(CH_3)_2$.

6. A compound as claimed in claim 1, wherein the compound is compound of Formula (A):

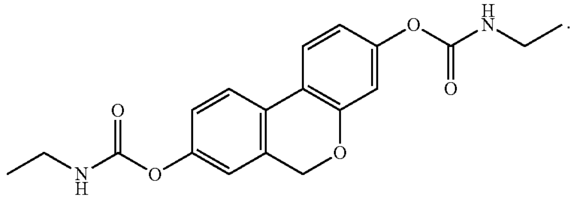 [SMILES: CCNC(=O)Oc1ccc2c(c1)COc1cc(OC(=O)NCC)ccc1-2]

7. A compound as claimed in claim 1, wherein the compound is compound of Formula (B):

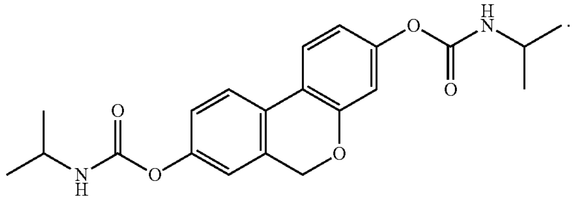 [SMILES: CC(C)NC(=O)Oc1ccc2c(c1)COc1cc(OC(=O)NC(C)C)ccc1-2]

8. A pharmaceutical composition comprising a compound or a pharmaceutically acceptable salt or solvate as defined in claim 1, and a pharmaceutically acceptable excipient.

9. A method of treatment or prevention of a disease, disorder or condition, the method comprising the step of administering an effective amount of a compound or a pharmaceutically acceptable salt or solvate as defined in claim 1, to thereby treat or prevent the disease, disorder or condition, wherein the disease, disorder or condition is selected from metabolic stress, cardiovascular disease, endothelial cell dysfunction, sarcopenia, muscle degenerative disease, Duchenne muscular dystrophy, alcoholic liver disease, non-alcoholic fatty liver disease, drug-induced liver injury, a 1-antitrypsin deficiency, ischemia/reperfusion injury, inflammation, aging of the skin. inflammatory bowel disease, Crohn's disease, obesity, metabolic syndrome, type II diabetes mellitus, hyperlipidemia, osteoarthritis, neurodegenerative disease, Alzheimer's disease, Huntington's disease, Parkinson's disease, amyotrophic lateral sclerosis, age-related macular degeneration, mitochondrial diseases, muscle diseases; sporadic inclusion body myositis (sIBM). anxiety disorder, cancer, cognitive disorder, stress, and mood disorder.

* * * * *